(12) United States Patent
Zhang et al.

(10) Patent No.: US 11,247,997 B2
(45) Date of Patent: Feb. 15, 2022

(54) COMPOUND AND PREPARATION AND APPLICATION THEREOF

(71) Applicant: Institute of Chemical Materials of China Academy of Engineering and Physics, Sichuan (CN)

(72) Inventors: Qinghua Zhang, Mianyang (CN); Mucong Deng, Mianyang (CN); Yongan Feng, Mianyang (CN)

(73) Assignee: INSTITUTE OF CHEMICAL MATERIALS OF CHINA ACADEMY OF ENGINEERING AND PHYSICS, Sichuan (CN)

( * ) Notice: Subject to any disclaimer, the term of this patent is extended or adjusted under 35 U.S.C. 154(b) by 189 days.

(21) Appl. No.: 16/480,674

(22) PCT Filed: Jan. 28, 2019

(86) PCT No.: PCT/CN2019/073473
§ 371 (c)(1),
(2) Date: Jul. 24, 2019

(87) PCT Pub. No.: WO2020/034601
PCT Pub. Date: Feb. 20, 2020

(65) Prior Publication Data
US 2021/0155624 A1    May 27, 2021

(30) Foreign Application Priority Data
Aug. 15, 2018 (CN) .......................... 201810929060.X

(51) Int. Cl.
*C07D 487/04* (2006.01)
*C06B 25/34* (2006.01)
(Continued)

(52) U.S. Cl.
CPC ............ *C07D 487/04* (2013.01); *C06B 25/34* (2013.01); *C07D 253/08* (2013.01);
(Continued)

(58) Field of Classification Search
CPC .. C07D 487/04; C07D 253/08; C07D 487/14; C07D 498/04; C07D 498/14; C06B 25/34
See application file for complete search history.

(56) References Cited

FOREIGN PATENT DOCUMENTS

| CN | 101492424 A | 7/2009 |
|---|---|---|
| CN | 101591356 A | 12/2009 |

(Continued)

OTHER PUBLICATIONS

Molchanova; Journal of Molecular Structure (Theochem), 1999, 465, 11-24. (Year: 1999).*

(Continued)

*Primary Examiner* — Daniel R Carcanague
(74) *Attorney, Agent, or Firm* — Pearne & Gordon LLP

(57) ABSTRACT

The present invention discloses a compound, which comprises the structure shown in FIG. 1; and further discloses a preparation method thereof, a precursor material used in the preparation method, explosives comprising the compound, and the application thereof in the field of explosives, in particular in the application of green environmentally-friendly primers. The compound disclosed by the invention may provide green environmental protection type primer, and meets the problem of requiring green environmental protection primers in many fields such as military industry, firework and civil explosion engineering. The compound disclosed in the invention has a simple preparation method and may be prepared by simple reaction steps and conditions, which has the advantages of being green and reliable as no pollution during the reaction process and use, no metal required in the compound structure, with good stability, high (Continued)

impact sensitivity, friction sensitivity, and initiation capability, and appropriate minimum initiating charge.

15 Claims, 7 Drawing Sheets

(51) Int. Cl.
   *C07D 253/08* (2006.01)
   *C07D 487/14* (2006.01)
   *C07D 498/04* (2006.01)
   *C07D 498/14* (2006.01)

(52) U.S. Cl.
   CPC ......... *C07D 487/14* (2013.01); *C07D 498/04* (2013.01); *C07D 498/14* (2013.01)

(56) References Cited

FOREIGN PATENT DOCUMENTS

| | | | | |
|---|---|---|---|---|
| CN | 103193560 | A | | 7/2013 |
| CN | 103373968 | A | | 10/2013 |
| CN | 105622615 | A | | 6/2016 |
| CN | 105949219 | A | | 9/2016 |
| CN | 105111213 | A | | 4/2017 |
| CN | 108299442 | A | | 7/2018 |
| CN | 108752349 | A | | 11/2018 |
| CN | 112079838 | A * | 12/2020 | |
| DE | 3222960 | A1 * | 12/1983 | ........... C07C 255/08 |

OTHER PUBLICATIONS

Chavez; Top Heterocycl Chem 2017, 53, 1-28. (Year: 2017).*
Dorwald; Side Reactions in Organic Synthesis, 2005, Wiley-VCH, Preface and Chapter 1, 32 pages. (Year: 2005).*
National Center for Biotechnology Information. "PubChem Compound Summary for CID 10608311" PubChem, https://pubchem.ncbi.nlm.nih.gov/compound/10608311. Create Date Oct. 25, 2006. (Year: 2006).*
Lei; Chemical Engineering Journal, 2021, 416, 1291902, 10 pages. DOI: 10.1016/j.cej.2021.129190 (Year: 2021).*
Liu; Organic Letters, 2021, 23, 734-738. DOI: 10.1021/acs.orglett.0c03952 (Year: 2021).*
Mitschker; Synthesis, 1988, 517-520. DOI: 10.1055/s-1988-27622 (Year: 1988).*
State Intellectual Property Office of the People's Republic of China (ISR/CN), "International Search Report for PCT/CN2019/073473", China, dated May 7, 2019.
State Intellectual Property Office of the People's Republic of China (ISR/CN), "Written Opinion of the International Searching Authority for PCT/CN2019/073473", China, dated May 7, 2019.
Lech Siefaniak, Nitrogen-14 nuclear magnetic resonance of azine-N-oxides, Spectrochimica Acta, vol. 32A, pp. 345-349, Dec. 31, 1976.
Boulton, A.J., et al, 1,2,3-Benzotriazine 2-Oxides, J. Chem. Soc. Perkin Trans 1, vol. 6, pp. 1509-1512, Dec. 31, 1988.
CAS Registry 1784648-12-9 (Jun. 19, 2015).
First Office Action of Priority Application CN201810929060.X, translation thereof (from Global Dossier), and translated first search, dated Jul. 29, 2019.
Second Office Action of Priority Application CN201810929060.X, translation thereof (from Global Dossier), and translated supplementary search, dated Nov. 15, 2019.
Yuan, J., Long, X., Zhang, C. "Influence of N-Oxide Introduction on the Stability of Nitrogen-Rich Heteroaromatic Rings: A Quantum Chemical Study". The Journal of Physical Chemistry A, 2016, vol. 120, Issue 47, pp. 9446-9457, Nov. 14, 2016.
Extended European Search Report of corresponding European Application EP19734222.3 dated Aug. 5, 2021, pp. 1-9.
Boulton et al. "1,2,3-Benzotriazinone 1-Oxides," J. Chem Soc. Perkin Trans. I, No. 3, 543-546, Jan. 1, 1989.

* cited by examiner

US 11,247,997 B2

COMPOUND AND PREPARATION AND APPLICATION THEREOF

CROSS-REFERENCE TO RELATED APPLICATIONS

This application is a U.S. national phase application of PCT Patent Application Serial No. PCT/CN2019/073473, filed on Jan. 28, 2019, and claims priority to and benefit of Chinese Patent Application No. 201810929060.X, filed on Aug. 15, 2018 in the State Intellectual Property Office of P.R. China, which are incorporated herein by reference in their entireties.

TECHNICAL FIELD

The present invention relates to the field of chemistry, and more particularly to a compound and a preparation method, a precursor, and an application thereof, and explosives having the compound.

BACKGROUND ART

As an important part of pyrotechnics and weapons, primers have always been an important scientific issue. However, its research has been slow for a long time compared to the development of modern pyrotechnics and weapons. For more than 100 years, lead azide and lead styphnate have remained the two types of primers mainly used in military pyrotechnics. With the increasing requirements for the safety of pyrotechnics for weapons, and ammunition, the defects of lead azide and lead styphnate in the performance are becoming more and more obvious.

Lead azide, with a high degree of mechanical sensitivity, could be directly detonated by slight stimulation under unconstrained conditions, with poor flame acupuncture sensitivity; and lead styphnate, with extremely sensitivity to static electricity, has only $10^{-4}$ J initiation energy by electrostatic discharge, both of which often lead to major accidents in the service and use of pyrotechnics and pharmaceuticals, and also hinder the development of advanced pyrotechnics.

From an environmental point of view, pyrotechnics are currently facing the dilemma that there is no green environmentally friendly primers are available. According to statistics, among the more than 20 kinds of qualitative elemental primers that have been produced, only two kinds of primers dinitrodiazophenol (DDNP) and tetrazene do not contain metal components, and potassium dinitrobenzofuroxan (KDNBF) contains light metal potassium. Other primers contain toxic metal components such as mercury, lead, antimony and cadmium. The DDNP, with a large amount of waste water generated in the synthesis process polluting the environment, is limited to the application in civil explosion engineering as detonator due to the large amount of limiting charge. Tetraazene is only used as a mechanical sensitizer and cannot be used alone, with a dosage of only 5% of the formulation. KDNBF is applied to the electric ignition head of the power source pyrotechnics in a very small amount due to the defects of initiation capability, sensitivity performance, fluidity and the like.

With the severe environment of modern war and the development of new initiating technology of pyrotechnics, it is difficult for the active explosives to meet the technical requirements of advanced pyrotechnics. In particular, no energetic materials applicable in precision strike and rapid-fire weapons ammunition fuze pyrotechnics, high-overload pyrotechnics, and lasers, semiconductor bridges, and slapper-plate pyrotechnics are available.

Therefore, in many fields such as military industry, pyrotechnics, and civil explosion engineering, a green environmentally-friendly primer is urgently needed.

SUMMARY OF THE INVENTION

In order to overcome the deficiencies of the prior art, the technical problem solved by the present invention is to provide a green environmental protection type primer, which satisfies the problem of requiring environmentally-friendly primers in many fields such as military industry, pyrotechnics, and civil explosion engineering.

In order to solve the above technical problems, the technical solutions adopted by the present invention are as follows:

A compound comprising a structure of formula shown in FIG. 1.

Preferably, the compound is a fused ring compound, the fused ring compound comprises at least the structure of formula shown in FIG. 1 and a polycyclic ring. More preferably, in the structure of formula shown in FIG. 1, $A_1$ and $A_2$ are selected from one or more types in carbon atoms, nitrogen atoms, oxygen atoms, phosphorus atoms and sulfur atoms. Wherein preferably, in the structure of formula shown in FIG. 1, $A_1$ and $A_2$ are selected from one or two types in carbon atoms and nitrogen atoms. More preferably, in the structure of formula shown in FIG. 1, $A_1$ and $A_2$ are carbon atoms. Same preferably, in the structure of formula shown in FIG. 1, one of $A_1$ and $A_2$ is a nitrogen atom and the other is a carbon atom. Preferably, in the structure of formula shown in FIG. 1, $A_1$ is a nitrogen atom and $A_2$ is a carbon atom.

Preferably, the compound is a fused ring compound comprising 2 to 3 rings. Wherein preferably, the compound is a fused ring compound comprising two rings. Same preferably, the compound is a fused ring compound comprising three rings. Preferably, the fused ring compound is a fused ring compound of the structure of formula shown in FIG. 1 and the polycyclic ring. Preferably, in the fused ring compound, the structure of formula shown in FIG. 1 and the polycyclic ring share two carbon atoms.

Preferably, the polycyclic ring is selected from one or more of a three-membered ring, a four-membered ring, a five-membered ring, a six-membered ring, a seven-membered ring, and an eight-membered ring. Also preferably, the polycyclic ring is selected from one or more of a five-membered ring, a six-membered ring and a seven-membered ring. Wherein preferably, the polycyclic ring is one or more of a five-membered ring and a six-membered ring. More preferably, the polycyclic ring is a five-membered ring. More preferably, the polycyclic ring is a six-membered ring. Same preferably, the polycyclic ring are plurality of polycyclic rings. On the other hand, preferably, the plurality of polycyclic rings comprise a five-membered ring and a six-membered ring. Wherein preferably, the plurality of polycyclic rings are a five-membered ring and a six-membered ring. More preferably, the polycyclic ring is composed of carbon atoms.

Preferably, the polycyclic ring is selected from one of a cyclopentadienyl ring, a benzene ring and a cycloheptatrienyl ring. Wherein preferably, the polycyclic ring is a benzene ring. Or preferably, the polycyclic ring is a heterocyclic ring, and the hetero atom of the heterocyclic ring comprises one selected from a group consisting of a nitrogen atom, an oxygen atom, a silicon atom, a phosphorus atom, a sulfur atom, an arsenic atom, a selenium atom, and a tellurium atom. Preferably, the hetero atoms comprises two selected from a group consisting of a nitrogen atom, an oxygen atom, a silicon atom, a phosphorus atom, a sulfur atom, an arsenic atom, a selenium atom and a tellurium atom. More preferably, the hetero atom is selected from one of a nitrogen atom, an oxygen atom, a silicon atom, a phosphorus atom, a sulfur atom, an arsenic atom, a selenium atom or a tellurium atom. More preferably, the hetero atom is a nitrogen atom or an oxygen atom. More preferably, the hetero atom is selected from one kind in nitrogen atoms and oxygen atoms. More preferably, the hetero atom is a nitrogen atom. Same preferably, the hetero atom is an oxygen atom. Preferably, the heterocyclic ring comprises 1, 2, 3, 4 or 5 heteroatoms. Wherein preferably, the heterocyclic ring comprises 1, 2, 3, 4 or 5 nitrogen atoms. Same preferably, the heterocyclic ring comprises 1 oxygen atom. Wherein preferably, the polycyclic ring is selected from one of furan, pyrrole, thiophene, imidazole, pyrazole, oxazole, thiazole, pyridine, pyrazine, pyrimidine, pyridazine, furazan, triazoles, tetrazoles, triazines and tetrazines. More preferably, the polycyclic ring is selected from one of imidazole, pyrazole, pyridine, pyrazine, pyrimidine, pyridazine, furazan, triazoles, tetrazoles, triazines and tetrazines. More preferably, the polycyclic ring is selected from one of imidazole, pyrazole, pyridine, pyrazine, furazan, triazoles, tetrazoles, triazines and tetrazines. More preferably, the polycyclic ring is selected from one of imidazole, pyrazole, pyridine and pyrazine.

Preferably, the polycyclic ring is selected from one of imidazole and pyrazole. More preferably, the polycyclic ring is pyrazole. Or preferably, the polycyclic ring is imidazole. Same preferably, the polycyclic ring is selected from one of pyridazine, pyridine and pyrazine. More preferably, the polycyclic ring is pyridazine. Or preferably, the polycyclic ring is pyridine. Or preferably, the polycyclic ring is pyrazine. Same preferably, the polycyclic ring is triazoles. More preferably, the polycyclic ring is 1,2,4-triazole. Same preferably, the polycyclic ring is triazines. More preferably, the polycyclic ring is 1,2,3-triazine. Or preferably, the polycyclic ring is 1,2,4-triazine. Same preferably, the polycyclic ring is selected from one of furan, furazan and oxazole. More preferably, the polycyclic ring is furan. Or preferably, the polycyclic ring is furazan.

Preferably, the polycyclic ring includes a substituent. More preferably, the substituent is selected from one of: saturated hydrocarbon groups, including an alkane group. functionalized saturated hydrocarbon groups, including a nitroalkane group, a gem-dinitroalkane group, a nitroform alkane group, and a halogenated alkane group, an alcohol group, an ether group, and a thioether group, a carboxylic acid group, an ester group, a nitrate group, a sulfonic acid group, and a sulfonate group, a ketone group, an amide group, and a hydrazide group, an aldehyde group, unsaturated aliphatic hydrocarbon groups, including an olefin group, an alkyne group, a halogenated alkene group, and a nitroalkyne group, unsaturated aromatic hydrocarbon groups, including a monocyclic aromatic hydrocarbon group, a polycyclic aromatic hydrocarbon group, a fused ring aromatic hydrocarbon group, a functionalized monocyclic aromatic hydrocarbon group, a functionalized polycyclic aromatic hydrocarbon group, and a functionalized fused aromatic hydrocarbon group, heterocyclic aromatic hydrocarbon groups, including thiophene, pyridine, furan, azole ring, azine ring, oxazole ring and a corresponding monofunctional or polyfunctional group thereof heterocyclic non-aromatic hydrocarbon groups, including an aza-bridged hydrocarbon group, and an oxa-bridged hydrocarbon group, halogen atoms, a cyano group, an oximido group, an amino group, an imino group, an azo group, an azoxy group, an azido group, and a hydrazine group, a hydroxyl group, a hydroxamino group, and an alkoxy group, a nitroamino group, a nitro group and a nitroso group. Wherein preferably, the substituent is selected from one of a nitro group, a nitroso group, a nitroamino group, a hydroxyamino group, a cyano group, an oximido group, an amino group, an imino group, an azo group, an azoxy group, an azido group, a hydrazine group, an aza-bridged hydrocarbon group, pyridazole ring, azine ring, a nitroalkane group, a gem-dinitroalkane group, a nitroform alkane group, and a nitroalkyne group. Same preferably, the substituent is selected from one of a hydroxyl group, a hydroxylamine group, an alkoxy group, an alcohol group, an ether group, a thioether group, a carboxylic acid group, an ester group, a nitrate group, a sulfonic acid group, a sulfonate group, a ketone group, an amide group, a hydrazide group, an aldehyde group, a nitroalkyne group, a nitroalkane group, a gem-dinitroalkane group, a nitroform alkane group, a furan group, oxazole ring, and an oxa-bridged hydrocarbon group. More preferably, the substituent is selected from one of a nitro group, a nitroso group, a nitroamino group, a nitroalkane group, a gem-dinitroalkane group, a nitroform alkane group, and a nitroalkyne group. More preferably, the substituent is selected from one of a nitro group and a nitroso group. More preferably, the substituent is a nitro group. Same preferably, the substituent is selected from one of an amino group, an imino group, a nitroamino group, a hydroxyamino group and a hydrazine group. More preferably, the substituent is selected from one of an amino group and an imino group. More preferably, the substituent is an amino group. Wherein preferably, the substituent is a nitroamino group. Same preferably, the substituent is selected from one of an azido group, an azo group, an azoxy group, and a hydrazine group. More preferably, the substituent is an azido group. Same preferably, the substituent is a halogen atom. More preferably, the substituent is selected from one of fluorine, chlorine, bromine and iodine. More preferably, the substituent is chlorine. On the other hand, preferably, the substituent is located on a carbon atom of the polycyclic ring.

Preferably, the substituent $R_1$ in the structure of formula shown in FIG. 1 is selected from one of hydrogen, amino group, nitro group, nitroamino group, azido group, fluorine, chlorine, bromine, iodine, $C_nH_m(NO_2)_p$, and the structure of formula shown in FIG. 2, wherein m+p=2n+1. More preferably, the substituent $R_1$ in the structure of formula shown in FIG. 1 is selected from one of an amino group, a nitro group, a nitroamino group, and an azido group. More preferably, the $R_1$ is an azido group. More preferably, the $R_1$ is an amino group. More preferably, the $R_1$ is a nitro group. More preferably, the $R_1$ is a nitroamino group. Same preferably, the $R_1$ is selected from one of fluorine, chlorine, bromine and iodine. More preferably, the $R_1$ is chlorine. Another preferably, the $R_1$ is a group selected from nitro group, nitroamino group or $C_nH_m(NO_2)_p$, wherein n and p are positive integers. More preferably, the $R_1$ is a group selected from nitro group, nitroamino group or $C_nH_m(NO_2)_p$, wherein m, n, p are positive integers. More preferably, the $R_1$ is a group selected from nitro group, nitroamino group or $C_nH_m(NO_2)_p$, wherein m, n, p are positive integers, and n=1, 2, 3 or 4.

On the other hand, preferably, in the structure of formula shown in FIG. 2, the $A_1$ to $A_5$ are selected from one or more types in carbon atoms, nitrogen atoms, oxygen atoms, phosphorus atoms and sulfur atoms. More preferably, in the structure of formula shown in FIG. 2, the $A_1$ to $A_5$ are selected from one, two or three types in carbon atoms, nitrogen atoms and oxygen atoms. More preferably, in the structure of formula shown in FIG. 2, the $A_1$ to $A_5$ are selected from one or two types in carbon atoms and nitrogen atoms. More preferably, in the structure of formula shown in FIG. 2, the $A_1$ to $A_5$ are carbon atoms. On the other hand, preferably, in the structure of formula shown in FIG. 2, the number of substituents on the $A_1$ to $A_5$ is 0, 1, 2, 3 or 4. And preferably, the $R_2$ is selected from one or more of hydrogen, amino group, nitro group, nitroamino group, azido group, fluorine, chlorine, bromine, iodine, $C_nH_m(NO_2)_p$, and the structure of formula shown in FIG. 2, wherein $m+p=2n+1$. Another preferably, the $R_2$ is a group selected from nitro group, nitroamino group or $C_nH_m(NO_2)_p$, wherein n and p are positive integers. More preferably, the $R_2$ is a group selected from nitro group, nitroamino group or $C_nH_m(NO_2)_p$, wherein m, n, and p are positive integers. More preferably, the $R_2$ is a group selected from nitro group, nitroamino group or $C_nH_m(NO_2)_p$, wherein m, n, p are positive integers, and n=1, 2, 3 or 4.

Preferably, the fused ring compound comprises at least a structure of formula shown in FIG. 3, wherein $A_1$ to $A_5$ are selected from one or more types in carbon atoms, nitrogen atoms, oxygen atoms, phosphorus atoms and sulfur atoms. More preferably, in the structure of formula shown in FIG. 3, the $A_1$ to $A_5$ are selected from one, two or three types in carbon atoms, nitrogen atoms and oxygen atoms. More preferably, in the structure of formula shown in FIG. 3, the $A_1$ to $A_5$ are selected from one or two types in carbon atoms and nitrogen atoms. Another preferably, in the structure of formula shown in FIG. 3, the $A_1$ to $A_2$ are carbon atoms. At the same time, preferably, in the structure of formula shown in FIG. 3, the $A_3$ to $A_5$ are selected from one, two or three types in carbon atoms, nitrogen atoms and oxygen atoms. More preferably, in the structure of formula shown in FIG. 3, the $A_3$ to $A_5$ are selected from one or two types in carbon atoms and nitrogen atoms. Wherein preferably, in the structure of formula shown in FIG. 3, the $A_1$ to $A_5$ comprise 0, 1, 2, 3, 4 or 5 nitrogen atoms, the remainder being carbon atoms. Wherein preferably, in the structure of formula shown in FIG. 3, the $A_3$ to $A_5$ comprise 0, 1, 2 or 3 nitrogen atoms, and the others being carbon atoms. Wherein preferably, in the structure of formula shown in FIG. 3, the $A_1$ to $A_5$ form a furazan ring. More preferably, in the structure of formula shown in FIG. 3, the $A_1$ to $A_2$ are carbon atoms, the $A_3$ and $A_5$ are nitrogen atoms, and the $A_4$ is an oxygen atom. More preferably, in the structure of the formula shown in FIG. 3, the $A_1$ to $A_2$ are carbon atoms, the $A_3$ and $A_5$ are nitrogen atoms, the $A_4$ is an oxygen atom, and the $A_3$ has an oxygen substituent and a coordinate bond is formed therebetween. Same preferably, in the structure of formula shown in FIG. 3, the $A_1$ to $A_5$ form a diazole ring. Wherein preferably, in the structure of formula shown in FIG. 3, the $A_1$ to $A_5$ form a pyrazole ring. More preferably, in the structure of formula shown in FIG. 3, the $A_1$, $A_2$ and $A_5$ are carbon atoms, and the $A_3$ and $A_4$ are nitrogen atoms. Wherein preferably, in the structure of formula shown in FIG. 3, the $A_5$ has a nitro substituent. Particularly preferably, in the structure of formula shown in FIG. 3, the $A_1$, $A_2$ and $A_5$ are carbon atoms, the $A_3$ and $A_4$ are nitrogen atoms, and in the structure of formula shown in FIG. 3, the $A_5$ has a nitro substituent. Same preferably, in the structure of formula shown in FIG. 3, the $A_1$ to $A_5$ form an imidazole ring. Wherein preferably, in the structure of formula shown in FIG. 3, the $A_1$, $A_2$ and $A_4$ are carbon atoms, and the $A_3$ and $A_5$ are nitrogen atoms. On the other hand, preferably, in the structure of formula shown in FIG. 3, the number of substituents on $A_1$ to $A_5$ is 0, 1, 2, 3 or 4. And preferably, the $R_3$ is selected from one or more of hydrogen, amino group, nitro group, nitroamino group, azido group, fluorine, chlorine, bromine, iodine, oxygen, $C_nH_m(NO_2)_p$, and the structure of formula shown in FIG. 2, wherein $m+p=2n+1$. Another preferably, the $R_3$ is a group selected from nitro group, nitroamino group or $C_nH_m(NO_2)_p$, wherein n and p are positive integers. More preferably, the $R_3$ is a group selected from nitro group, nitroamino group or $C_nH_m(NO_2)_p$, wherein m, n, and p are positive integers. More preferably, the $R_3$ is a group selected from nitro group, nitroamino group or $C_nH_m(NO_2)_p$, wherein m, n, p are positive integers, and n=1, 2, 3 or 4.

Preferably, the fused ring compound comprises at least a structure of formula shown in FIG. 4, wherein $A_1$ to $A_6$ are selected from one or more types in carbon atoms, nitrogen atoms, oxygen atoms, phosphorus atoms and sulfur atoms. More preferably, in the structure of formula shown in FIG. 4, the $A_1$ to $A_6$ are selected from one or two types in carbon atoms and nitrogen atoms. Another preferably, in the structure of formula shown in FIG. 4, the $A_1$ to $A_2$ are carbon atoms. At the same time, preferably, in the structure of formula shown in FIG. 4, the $A_3$ to $A_6$ are selected from one or two types in carbon atoms and nitrogen atoms. Wherein preferably, in the structure of formula shown in FIG. 4, the $A_1$ to $A_6$ comprise 0, 1, 2, 3, 4, 5 or 6 nitrogen atoms, the remainder being carbon atoms. Wherein preferably, in the structure of formula shown in FIG. 4, the $A_3$ to $A_6$ comprise 0, 1, 2, 3 or 4 nitrogen atoms, the remainder being carbon atoms. Particularly preferably, in the structure of formula shown in FIG. 4, the $A_1$ to $A_6$ are carbon atoms. Same preferably, in the structure of formula shown in FIG. 4, the $A_4$ and $A_5$ are nitrogen atoms. More preferably, in the structure of formula shown in FIG. 4, the $A_1$ to $A_3$ and $A_6$ are carbon atoms, and $A_4$ and $A_5$ are nitrogen atoms. Same preferably, in the structure of formula shown in FIG. 4, the $A_3$ to $A_5$ are nitrogen atoms. More preferably, in the structure of formula shown in FIG. 4, the $A_1$ to $A_2$ and $A_6$ are carbon atoms, and $A_3$ to $A_5$ are nitrogen atoms. Particularly preferably, in the structure of formula shown in FIG. 4, the $A_1$ to $A_2$ and $A_6$ are carbon atoms, $A_3$ to $A_5$ are nitrogen atoms, the $A_4$ has an oxygen substituent and a coordinate bond is formed therebetween, and the $A_6$ has an azido substituent. On the other hand, preferably, in the structure of formula shown in FIG. 4, the number of substituents on $A_1$ to $A_6$ is 0, 1, 2, 3, 4 or 5 in total. And preferably, the $R_4$ is selected from or more one of hydrogen, amino group, nitro group, nitroamino group, azido group, fluorine, chlorine, bromine, iodine, oxygen, $C_nH_m(NO_2)_p$, and the structure of formula shown in FIG. 2, wherein $m+p=2n+1$. Another preferably, the $R_4$ is selected from one of nitro group, nitroamino group or $C_nH_m(NO_2)_p$, wherein n and p are positive integers. More preferably, the $R_4$ is a group selected from nitro group, nitroamino group or $C_nH_m(NO_2)_p$, wherein m, n, and p are positive integers. More preferably, the $R_4$ is a group selected from nitro group, nitroamino group or $C_nH_m(NO_2)_p$, wherein m, n, p are positive integers, and n=1, 2, 3 or 4.

Preferably, the fused ring compound comprises at least a structure of formula shown in FIG. 5, wherein $A_1$ to $A_9$ are selected from one or more types in carbon atoms, nitrogen atoms, oxygen atoms, phosphorus atoms and sulfur atoms. More preferably, in the structure of formula shown in FIG. 5, the $A_1$ to $A_9$ are selected from one, two or three types in carbon atoms, nitrogen atoms and oxygen atoms. More preferably, in the structure of formula shown in FIG. 5, the $A_1$ to $A_9$ are selected from one or two types in carbon atoms and nitrogen atoms. Another preferably, in the structure of formula shown in FIG. 5, the $A_1$ to $A_2$ are carbon atoms. At the same time, preferably, in the structure of formula shown in FIG. 5, the $A_3$ to $A_9$ are selected from one, two or three types in carbon atoms, nitrogen atoms and oxygen atoms. More preferably, in the structure of formula shown in FIG. 5, the $A_3$ to $A_9$ are elected from one or two types in carbon atoms and nitrogen atoms. Wherein preferably, in the structure of formula shown in FIG. 5, the $A_1$ to $A_9$ comprise 0, 1, 2, 3, 4, 5, 6, 7, 8 or 9 nitrogen atoms, the remainder being carbon atoms. Wherein preferably, in the structure of formula shown in FIG. 5, the $A_1$ to $A_6$ comprise 0, 1, 2, 3, 4, 5 or 6 nitrogen atoms, the remainder being carbon atoms. Same preferably, in the structure of formula shown in FIG. 5, the $A_4$, $A_5$, $A_7$ to $A_9$ comprise 0, 1, 2, 3, 4 or 5 nitrogen atoms, the remainder being carbon atoms. Wherein preferably, in the structure of formula shown in FIG. 5, the $A_4$, $A_5$, $A_7$ to $A_9$ form a furazan ring. Same preferably, in the structure of formula shown in FIG. 5, the $A_4$, $A_5$, $A_7$ to $A_9$ form a triazole ring. More preferably, in the structure of formula shown in FIG. 5, the $A_4$, $A_5$, $A_7$ to $A_9$ form a 1,2,4-triazole ring. Same preferably, in the structure of formula shown in FIG. 5, the $A_1$ to $A_6$ form a diazine ring. More preferably, in the structure of formula shown in FIG. 5, the $A_1$ to $A_6$ form a pyrazine ring. Same preferably, in the structure of formula shown in FIG. 5, the $A_1$ to $A_6$ form a triazine ring. More preferably, in the structure of formula shown in FIG. 5, the $A_1$ to $A_6$ form a 1,2,4-triazine ring. More preferably, in the structure of formula shown in FIG. 5, the $A_4$, $A_5$, $A_7$ to $A_9$ form a furazan ring, and the $A_1$ to $A_6$ form a diazine ring. Particularly preferably, in the structure of formula shown in FIG. 5, the $A_1$, $A_2$, $A_4$, and $A_5$ are carbon atoms, the $A_3$, $A_6$, $A_7$, and $A_9$ are nitrogen atoms, and the $A_8$ is an oxygen atom. Same preferably, in the structure of formula shown in FIG. 5, the $A_4$, $A_5$, $A_7$ to $A_9$ form a triazole ring, and the $A_1$ to $A_6$ form a triazine ring. More preferably, in the structure of formula shown in FIG. 5, the $A_4$, $A_5$, $A_7$ to $A_9$ form a 1,2,4-triazole ring, and the $A_1$ to $A_6$ form a 1,2,4-triazine ring. Particularly preferably, in the structure of formula shown in FIG. 5, the $A_2$, $A_3$, $A_5$, and $A_8$ are carbon atoms, and the $A_1$, $A_4$, $A_6$, $A_7$, and $A_9$ are nitrogen atoms. On the other hand, preferably, in the structure of formula shown in FIG. 5, the number of substituents on $A_1$ to $A_6$ is 0, 1, 2, 3, 4 or 5 in total. More preferably, in the structure of formula shown in FIG. 5, the number of substituents on $A_4$, $A_5$, $A_7$ to $A_9$ is 0, 1, 2, 3 or 4 in total. And preferably, the $R_5$ is selected from one or more of hydrogen, amino group, nitro group, nitroamino group, azido group, fluorine, chlorine, bromine, iodine, oxygen, $C_nH_m(NO_2)_p$, and the structure of formula shown in FIG. 2, wherein m+p=2n+1. Another preferably, the $R_5$ is a group selected from nitro group, nitroamino group or $C_nH_m(NO_2)_p$, wherein n and p are positive integers. More preferably, the $R_5$ is a group selected from nitro group, nitroamino group or $C_nH_m(NO_2)_p$, wherein m, n, p are positive integers. More preferably, the $R_5$ is a group selected from nitro group, nitroamino group or $C_nH_m(NO_2)_p$, wherein m, n, p are positive integers, and n=1, 2, 3 or 4.

Preferably, the fused ring compound comprises the structure of formula shown in FIG. 1 and 3-nitropyrazole. More preferably, the compound is a structure of formula shown in FIG. 8. More preferably, the compound is a structure of formula shown in FIG. 7. More preferably, the analytical results of the structure of formula shown in FIG. 7 are as follows: DSC (160° C., 50° C.-250° C., 5° C.·min$^{-1}$). $^1$H NMR (400 MHz, DMSO-d$_6$, 25° C.) δ(ppm): 14.51 (brs, 1H, NH). $^{13}$C NMR (100 MHz, DMSO-d$_6$, 25° C.) δ(ppm): 157.95, 157.31, 148.07, 90.03. IR (KBr, γ/cm$^{-1}$): 3414 (m). 3231 (m). 2154 (s). 1600 (s). 1543 (s). 1403 (s). 1384 (s). 1313 (m). 1209 (m). 1131 (m). elemental analysis $C_4HN_9O_3$ (%): measured value (calculated value) C, 21.62; (21.53), H, 0.47; (0.45), N, 56.61; (56.50), O, 21.22; (21.51).

Preferably, the compound is a structure of formula shown in FIG. 13; or preferably, the compound is a structure of formula shown in FIG. 15; or preferably, the compound is a structure of formula shown in FIG. 17; or preferably, the compound is a structure of formula shown in FIG. 19; or preferably, the compound is a structure of formula shown in FIG. 21; or preferably, the compound is a structure of formula shown in FIG. 23; or preferably, the compound is a structure of formula shown in FIG. 25; or preferably, the compound is a structure of formula shown in FIG. 27. Wherein preferably, the $R_1$ in the structure of formulas shown in preceding figures is selected from one of hydrogen, amino group, nitro group, nitroamino group, azido group, fluorine, chlorine, bromine, iodine, $C_nH_m(NO_2)_p$, and the structure of formula shown in FIG. 2, wherein m+p=2n+1. More preferably, the $R_1$ in the structure of formulas shown in preceding figures is selected from one of an amino group, a nitro group, a nitroamino group, and an azido group.

More preferably, the $R_1$ in the structure of formulas shown in preceding figures is an azido group. More preferably, the $R_1$ in the structure of formulas shown in preceding figures is an amino group. More preferably, the $R_1$ in the structure of formulas shown in preceding figures is a nitro group. More preferably, the $R_1$ in the structure of formulas shown in preceding figures is a nitroamino group. Another preferably, the $R_1$ in the structure of formulas shown in preceding figures is a group selected from nitro group, nitroamino group or $C_nH_m(NO_2)_p$, wherein n and p are positive integers. More preferably, the $R_1$ in the structure of formulas shown in preceding figures is a group selected from nitro group, nitroamino group or $C_nH_m(NO_2)_p$, wherein m, n, p are positive integers. More preferably, the $R_1$ in the structure of formulas shown in preceding figures is a group selected from nitro group, nitroamino group or $C_nH_m(NO_2)_p$, wherein m, n, p are positive integers, and n=1, 2, 3 or 4. Another preferably, the $R_1$ in the structure of formula (G') is selected from one of hydrogen, amino group, nitro group, nitroamino group, azido group, fluorine, chlorine, bromine, iodine, $C_nH_m(NO_2)_p$, and the structure of formula shown in FIG. 2, wherein m+p=2n+1. More preferably, the $R_3$ in the structure of formula shown in FIG. 8 is selected from one or more of hydrogen, amino group, nitro group, nitroamino group, azido group, fluorine, chlorine, bromine, iodine, oxygen, $C_nH_m(NO_2)_p$ and the structure of formula shown in FIG. 2, wherein m+p=2n+1. More preferably, the $R_3$ in the structure of formula shown in FIG. 8 is a nitro group.

Or preferably, the fused ring compound comprises the structure of formula shown in FIG. 1 and 2-furoxan. Or preferably, the fused ring compound comprises two of the structures of the formula shown in FIG. 1; more preferably, the fused ring compound comprises two identical structures of the formula shown in FIG. 1; more preferably, the fused ring compound comprises two structures of the formula shown in FIG. 1, the two structures of the formula shown in FIG. 1 sharing $A_1$ and $A_2$.

Or preferably, the compound comprises a structure shown in FIG. 12, 14, 16, 18, 20, 22, 24 or 26. More preferably, the compound is a structure shown in FIG. 12, 14, 16, 18, 20, 22, 24 or 26.

The present invention further discloses a precursor in the preparation method of the compound. Specifically, the precursor is a compound characterized by comprising the structure shown in FIG. 6:

Preferably, in the structure shown in FIG. 6, $A_{10}$ and $A_{11}$ are selected from one or more types in carbon atoms, nitrogen atoms, oxygen atoms, phosphorus atoms and sulfur atoms. More preferably, in the structure shown in FIG. 6, $A_{10}$ and $A_{11}$ are selected from one or two types in carbon atoms and nitrogen atoms. Same preferably, in the structure shown in FIG. 6, $A_{10}$ and $A_{11}$ are carbon atoms. Same preferably, in the structure shown in FIG. 6, one of $A_{10}$ and $A_{11}$ is a nitrogen atom, and the other is a carbon atom.

Preferably, the compound comprises a polycyclic ring. More preferably, the polycyclic ring is selected from one or more of a three-membered ring, a four-membered ring, a five-membered ring, a six-membered ring, a seven-membered ring, and an eight-membered ring. More preferably, the polycyclic ring is selected from one or more of a five-membered ring, a six-membered ring and a seven-membered ring. More preferably, the polycyclic ring is one or more of a five-membered ring and a six-membered ring. More preferably, the polycyclic ring is a five-membered ring. Same preferably, the polycyclic ring is a six-membered ring.

Preferably, the polycyclic ring is composed of carbon atoms. More preferably, the polycyclic ring is selected from one of a cyclopentadienyl ring, a benzene ring and a cycloheptatrienyl ring.

More preferably, the polycyclic ring is a benzene ring. Or preferably, the polycyclic ring is a heterocyclic ring, and the hetero atom of the heterocyclic ring comprises one selected from a group consisting of a nitrogen atom, an oxygen atom, a silicon atom, a phosphorus atom, a sulfur atom, an arsenic atom, a selenium atom, and a tellurium atom. More preferably, the hetero atoms comprises two selected from a group consisting of a nitrogen atom, an oxygen atom, a silicon atom, a phosphorus atom, a sulfur atom, an arsenic atom, a selenium atom and a tellurium atom. Or preferably, the hetero atom is one of a nitrogen atom, an oxygen atom, a silicon atom, a phosphorus atom, a sulfur atom, an arsenic atom, a selenium atom or a tellurium atom. More preferably, the hetero atom is a nitrogen atom or an oxygen atom. Preferably, the hetero atom is selected from one kind in nitrogen atoms and oxygen atoms. More preferably, the hetero atom is a nitrogen atom. Wherein preferably, the polycyclic ring is selected from one of furan, pyrrole, thiophene, imidazole, pyrazole, oxazole, thiazole, pyridine, pyrazine, pyrimidine, pyridazine, furazan, triazoles, tetrazoles, triazines and tetrazines. More preferably, the polycyclic ring is selected from one of imidazole, pyrazole, pyridine, pyrazine, pyrimidine, pyridazine, furazan, triazoles, tetrazoles, triazines and tetrazines. More preferably, the polycyclic ring is selected from one of imidazole, pyrazole, pyridine, pyrazine, furazan, triazoles, tetrazoles, triazines and tetrazines. More preferably, the polycyclic ring is selected from one of imidazole, pyrazole, pyridine and pyrazine. More preferably, the polycyclic ring is selected from one of imidazole and pyrazole. More preferably, the polycyclic ring is pyrazole. Or preferably, the polycyclic ring is selected from one of pyridazine, pyridine and pyrazine. More preferably, the polycyclic ring is pyridazine. Or preferably, the polycyclic ring is tetrazoles.

Preferably, the polycyclic ring includes a substituent. More preferably, the substituent is selected from one of: saturated hydrocarbon groups, including an alkane group. functionalized saturated hydrocarbon groups, including a nitroalkane group, a gem-dinitroalkane group, a nitroform alkane group, and a halogenated alkane group. an alcohol group. an ether group, a thioether group. a carboxylic acid group, an ester group, a nitrate group, a sulfonic acid group, and a sulfonate group. a ketone group, an amide group, and a hydrazide group. an aldehyde group. unsaturated aliphatic hydrocarbon groups, including an olefin group, an alkyne group, a halogenated alkene group, and a nitroalkyne group. unsaturated aromatic hydrocarbon groups, including a monocyclic aromatic hydrocarbon group, a polycyclic aromatic hydrocarbon group, a fused ring aromatic hydrocarbon group, a functionalized monocyclic aromatic hydrocarbon group, a functionalized polycyclic aromatic hydrocarbon group, and a functionalized fused aromatic hydrocarbon group. heterocyclic aromatic hydrocarbon groups, including thiophene, pyridine, furan, azole ring, azine ring, oxazole ring and a corresponding monofunctional or polyfunctional group thereof heterocyclic nonaromatic hydrocarbon groups, including an aza-bridged hydrocarbon group, and an oxa-bridged hydrocarbon group. halogen atoms. a cyano group, an oximido group. an amino group, an imino group, an azo group, an azoxy group, an azido group, a hydrazine group. a hydroxyl group, a hydroxamino group, and an alkoxy group. a nitroamino group. a nitro group and a nitroso group. More preferably, the substituent is selected from one of a nitro group, a nitroso group, a nitroamino group, a hydroxyamino group, a cyano group, an oximido group, an amino group, an imino group, an azo group, an azoxy group, an azido group, a hydrazine group, an aza-bridged hydrocarbon group, pyridazole ring, azine ring, a nitroalkane group, a gem-dinitroalkane group, a nitroform alkane group, and a nitroalkyne group. More preferably, the substituent is selected from one of a cyano group and an oximido group. Or preferably, the substituent is selected from one of an amino group, an imino group, a nitroamino group, a hydroxyamino group and a hydrazine group. More preferably, the substituent is selected from one of an amino group and an imino group. More preferably, the substituent is an amino group. On the other hand, preferably, the substituent is located on a carbon atom of the polycyclic ring.

Preferably, the compound comprises the structure of 3-amino-4-cyanopyrazole. Same preferably, the compound comprises the structure of 4-amino-5-cyanoimidazole. Same preferably, the compound comprises the structure of 1-amino-2-cyanobenzene.

Preferably, the compound comprises the structure of 4-amino-5-cyanopyridazine. Same preferably, the compound comprises the structure of 3,3-diamino-2-(1H-tetrazol-5-yl)propanenitrile. Same preferably, the compound is 3-amino-4-cyanopyrazole. Same preferably, the compound is 4-amino-5-cyanoimidazole. Same preferably, the compound is 1-amino-2-cyanobenzene. Same preferably, the compound is 4-amino-5-cyanopyridazine. Same preferably, the compound is 3,3-diamino-2-(1H-tetrazol-5-yl)propanenitrile.

The present invention further discloses a method for preparing a compound, comprising: dispersing the precursor (the compound comprising the structure shown in FIG. 6) in a solvent; adding salts and azides, reacting at a first reaction temperature for a first reaction time; adding an acid; performing purification to obtain an intermediate; adding the intermediate to a nitration system, and performing nitration at a second temperature for a second reaction time; terminating the nitration reaction; and performing purification.

Preferably, the compound comprising the structure shown in FIG. 6 is the preferably precursor mentioned above. On the other hand, preferably, the intermediate is 3-amino-4-[1H-tetrazole]-1H-pyrazole. Preferably, the method for preparing the compound is the preparation method of the compound disclosed in present invention and comprises the structure shown in FIG. 1; more preferably, the method for preparing the compound is the preparation method of the compound disclosed in present invention and comprises the structure shown in FIG. 1 as preferable which mentioned above.

Preferably, the solvent is one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, or the like, or a mixture of two or more thereof. Wherein preferably, the ratio of the volume of solvent to the mass of compound comprising the structure shown in FIG. 6 is from 2 mL/g to 2 mL/mg.

Preferably, the salts are compounds of the formula $M_aX_b$, wherein M is one of Fe, Co, Ni, Mn, Zn, Cd, Au, Ag, Cu, Cr, Al, V, $NH_4$, $(CH_3)_2NH_2$, $(CH_3)_3NH$, $(CH_3CH_2)_2NH_2$ and $(CH_3CH_2)_3NH$, or a mixture of two or more thereof. and X is one of F, Cl, Br, I, $NO_3$, $SO_4$, $HSO_4$, $CO_3$, $HCO_3$, HCOO, $CH_3COO$, $CF_3COO$, $(COO)_2$ and $CH_2(COO)_2$, or a mixture of two or more thereof. Wherein preferably, the molar ratio of the salts to the compound comprising the structure shown in FIG. 6 is from 1:1 to 6:1. More preferably, the molar ratio of the salts to the compound comprising the structure shown in FIG. 6 is from 20:9 to 50:9. On the other hand, preferably, the azides are compounds of the general formula $R_a(N_3)_b$, wherein R is selected from one of Li, Na, K, Rb, Cu, Fe, Ag, Au, Pb, Cd, Ni and H, or a mixture of two or more thereof. More preferably, the molar ratio of the azides to the compounds comprising the structure shown in FIG. 6 is from 1:1 to 6:1. On the other hand, preferably, the first temperature is a temperature between −20° C. and 130° C. More preferably, the first temperature is a temperature between −10° C. and 130° C. Another preferably, the first reaction time is between 2 hours and 24 hours. More preferably, the first reaction time is between 2 hours and 10 hours. More preferably, the first reaction time is between 2 hours and 8 hours.

Preferably, the acid is any one or more of nitric acid, sulfuric acid, hydrochloric acid, hydrobromic acid, hydrofluoric acid, hydroiodic acid, formic acid, acetic acid, acetic anhydride, oxalic acid, malonic acid and trifluoroacetic acid. Another preferably, wherein the addition of the acid is to adjust the reaction system to a first pH value, the first pH value being between 1 and 4. More preferably, the first pH value is between 1.0 and 3.5. More preferably, the first pH value is between 2.0 and 3.0.

Preferably, the nitration system is fuming nitric acid, 100% nitric acid, dinitrogen pentoxide, nitronium tetrafluoroborate, 100% nitric acid/trifluoroacetic anhydride, 100% nitric acid/concentrated sulfuric acid, fuming nitric acid, 100% nitric acid/acetic anhydride, fuming nitric acid/concentrated sulfuric acid, fuming nitric acid/acetic anhydride, fuming nitric acid/trifluoroacetic anhydride, fuming nitric acid/acetic anhydride, sulfur trioxide/nitric acid, phosphorus pentoxide/nitric acid, fuming sulfuric acid/fuming nitric acid or fuming sulfuric acid/100% nitric acid. Wherein preferably, the nitration system is 100% nitric acid, 100% nitric acid/acetic anhydride, 100% nitric acid/trifluoroacetic anhydride, nitric acid/acetic anhydride, 100% nitric acid/concentrated sulfuric acid, fuming nitric acid, fuming nitric acid/concentrated sulfuric acid, fuming nitric acid/acetic anhydride, fuming nitric acid/trifluoroacetic anhydride, dinitrogen pentoxide, sulfur trioxide/nitric acid, phosphorus pentoxide/nitric acid, fuming sulfuric acid/fuming nitric acid or fuming sulfuric acid/100% nitric acid, the ratio of the mass of intermediate to the volume of nitration system is 1 g:5 mL to 1 g:50 mL. Same preferably, the nitration system is nitronium tetrafluoroborate, and the molar ratio of the volume of the intermediate to the nitration system is 1:1 to 1:50. On the other hand, preferably, the second temperature is a temperature between −20° C. and 130° C. More preferably, the second temperature is a temperature between −20° C. and 110° C. More preferably, the second temperature is a temperature between −20° C. and 100° C. More preferably, the second temperature is a temperature between −20° C. and room temperature. More preferably, the second temperature is room temperature.

Preferably, the second temperature is a temperature between 40° C. and 80° C. More preferably, the second temperature is a temperature between 50° C. and 70° C. Another preferably, the second reaction time is from 0.5 hour to 48 hours. More preferably, the second reaction time is 0.5 hour to 12 hours. More preferably, the second reaction time is 1 hours to 4 hours. Another preferably, the termination of the nitration reaction is to add the obtained product to the ice water.

Preferably, the method further comprises dispersing the obtained product after terminating the nitration reaction in a solvent, and introducing chlorine gas flow. More preferably, the chlorine gas flow is insoluble or poorly soluble in the solvent. Or preferably, the reaction temperature of the chlorine gas flow is between 30° C. and 100° C. More preferably, the reaction temperature of the chlorine gas flow is between 50° C. and 90° C. More preferably, the reaction temperature of the chlorine gas flow is between 60° C. and 70° C. Or preferably, the reaction time for introducing the chlorine gas flow is between 1 hour and 10 hours. More preferably, the reaction time for introducing the chlorine gas flow is between 1 hour and 5 hours. More preferably, the reaction time for introducing the chlorine gas flow is between 1 hour and 3 hours.

Preferably, the method further comprises dispersing the obtained product after terminating the nitration reaction in a solvent, adding a strong ammonia solution for reflux reaction. More preferably, the strong ammonia solution is dissolved in the solvent. Or preferably, the strong ammonia solution has a concentration of between 10% and 32%. Or preferably, the ratio of mass of the obtained product after the termination of the nitration reaction to the volume of concentrated aqueous ammonia is between 1 g:1 mL and 1 g:100 mL. More preferably, the ratio of mass of the obtained product after the termination of the nitration reaction to the volume of concentrated aqueous ammonia is between 1 g:5 mL and 1 g:20 mL. More preferably, the ratio of mass of the obtained product after the termination of the nitration reaction to the volume of concentrated aqueous ammonia is between 1 g:6 mL and 1 g:12 mL. Or preferably, the time for reflux reaction is from 0.5 hour to 24 hours. More preferably, the time for reflux reaction is between 1 hour and 12 hours. More preferably, the time for reflux reaction is between 2 hours and 8 hours.

Preferably, the method further comprises adding the product which is obtained by adding the strong ammonia solution for reflux reaction to an oxidizing solution. Wherein preferably, the oxidizing solution is selected from one or more of a mixed solution of concentrated sulfuric acid and 30% hydrogen peroxide, a mixed solution of concentrated sulfuric acid and 50% hydrogen peroxide, a mixed solution of concentrated sulfuric acid and trifluoroacetic acid, and a mixed solution of concentrated sulfuric acid and peracetic acid, and a mixed solution of concentrated sulfuric acid and acetic anhydride. Or preferably, the reaction time for adding the oxidizing solution is between 0.5 hour and 12 hours.

More preferably, the reaction time for adding the oxidizing solution is between 0.5 hour and 4 hours.

Preferably, the method further comprises: after the adding the strong ammonia solution for reflux reaction, adding the obtained product to another nitration system, and performing nitration reaction at another second temperature for another second reaction times.

Preferably, the method further comprises dispersing malononitrile and nitrite in a solvent. Wherein preferably, the nitrite is a compound of formula $MNO_2$, wherein M is selected from one of $NH_4$, Li, Na, K, Rb and Cs, or a mixture of two or more thereof. Or preferably, the solvent is any one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, or the like, or a mixture of two or more thereof.

Preferably, the method further comprises adding hydroxylamine compounds. Wherein preferably, the hydroxylamine compounds are hydroxylamine salts. Wherein preferably, the hydroxylamine salts are compounds of formula $(NH_3OH)_aX_b$, wherein X is selected from one of F, Cl, Br, I, $NO_3$, $SO_4$, $HSO_4$, $CO_3$, $HCO_3$, HCOO, $CH_3COO$, $CF_3COO$, $(COO)_2$ and $CH_2(COO)_2$, or a mixture of two or more thereof. More preferably, the hydroxylamine compounds are hydroxylamine halide salts. More preferably, the hydroxylamine compound is hydroxylamine hydrochloride. Or preferably, the reaction temperature of adding the hydroxylamine compound is a temperature between −20° C. and 130° C. More preferably, the reaction temperature of adding the hydroxylamine compound is a temperature between −20° C. and 40° C. More preferably, the reaction temperature of adding the hydroxylamine compound is a temperature between −10° C. and 40° C. Or preferably, the reaction time for adding the hydroxylamine compound is between 2 hours and 24 hours. More preferably, the reaction time for adding the hydroxylamine compound is between 2 hours and 10 hours. More preferably, the reaction time for adding the hydroxylamine compound is between 3 hours to 5 hours.

Preferably, the method further comprises adding alkalis and ester compounds after adding the hydroxylamine compounds. Wherein preferably, the alkalis are compounds of formula $M_a(OH)_b$, wherein M is selected from one of $NH_4$, Li, Na, K, Rb, Cs, Ca, Sr, Ba, or a mixture of two or more thereof. On the other hand, preferably, the ester compounds are compounds of the formula $R'COOR^2$, wherein $R^1$ and $R^2$ are selected from one of methyl, ethyl, propyl, isopropyl, butyl, sec-butyl, tert-butyl, and various pentyls and various hexyls, or a mixture of two or more thereof.

Preferably, the method further comprises adding an acid and lead dioxide after adding the alkalis and ester compounds. Preferably, the method further comprises adding concentrated hydrochloric acid for reflux reaction. Preferably, the method further comprises dissolving the obtained product in thionyl chloride and adding N,N-dimethylformamide for reflux reaction. Preferably, the method further comprises adding nitrides. Wherein preferably, the nitrides are compounds of the general formula $R_a(N)_b$, wherein R is selected from one of Li, Na, K, Rb, Cu, Fe, Ag, Au, Pb, Cd, Ni and H, or a mixture of two or more thereof. Preferably, the method further comprises adding nitroacetonitrile compounds. Wherein preferably, the nitroacetonitrile compounds are nitroacetonitrile salts. Wherein preferably, the nitroacetonitrile compounds are compounds of the general formula $M_a(CH(NO_2)CN)_b$, wherein M is selected from one of Li, Na, K, Rb, Cs, or a mixture of two or more thereof. Wherein preferably, the nitroacetonitrile compound is sodium nitroacetonitrile.

Preferably, the method comprises the following steps:

Step 1: synthesis of 3-amino-4-[1H-tetrazole]-1H-pyrazole: dispersing 3-amino-4-cyanopyrazole in a solvent at a certain temperature, adding specific salts ($M_aX_b$) and azides in batches, then continuing the reaction at a certain temperature, adding dropwise acid thereto, followed by filtration and washing, and drying the solid to obtain white powder, i.e., 3-amino-4-[1H-tetrazole]-1H-pyrazole. Preferably, the reaction temperature in step 1 is −10° C. to 130° C. Preferably, the solvent in step 1 is any one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, and xylene. the ratio of the volume of solvent to the mass of 3-amino-4-cyanopyrazole is 2 mL/g to 20 mL/g. Preferably, the ratio of amount of substance of the salts in the step 1 is $n(M_aX_b)$:n(3-amino-4-[1H-tetrazolyl]-1H-pyrazole)=1:1 to 6:1. the composition of the salts is: M=Fe, Co, Ni, Mn, Zn, Cd, Au, Ag, Cu, Cr, Al, V, $NH_4$, $(CH_3)_2NH_2$, $(CH_3)_3NH$, $(CH_3CH_2)_2NH_2$ or $(CH_3CH_2)_3NH$, X=F, Cl, Br, I, $NO_3$, $SO_4$, $HSO_4$, $CO_3$, $HCO_3$, HCOO, $CH_3COO$, $CF_3COO$, $(COO)_2$ or $CH_2(COO)_2$. Preferably, the ratio of amount of substance of azides used in step 1 is $n(R_a(N3)_b)$: n(3-amino-4-[1H-tetrazolyl]-1H-pyrazole)=1:1 to 6:1. R in the azides is: R=Li, Na, K, Rb, Cu, Fe, Ag, Au, Pb, Cd, Ni or H. Preferably, the acid in step 1 is any one or a mixture of: nitric acid, sulfuric acid, hydrochloric acid, hydrobromic acid, hydrofluoric acid, hydroiodic acid, formic acid, acetic acid, acetic anhydride, oxalic acid, malonic acid or trifluoroacetic acid, and the pH of the solution can adjusted to be 1-4 with the acid in the amount.

Step 2: synthesis of 4-azido-5-nitro-7H-pyrazolo[3,4-d][1,2,3]triazine-2-oxide: adding 3-amino-4-1H-tetrazole-pyrazole to a nitration system slowly, after the addition, controlling the temperature of the reaction system, performing nitration for 0.5 hour to 48 hours, then pouring the reaction system into ice, followed by filtration and washing, and drying to obtain white powder 4-azido-5-nitro-7H-pyrazolo[3,4-d][1,2,3]triazine-2-oxide. Preferably, the nitration system used in step 2 is commercially available fuming nitric acid or 100% nitric acid, or other nitration system, including nitrogen pentoxide, nitronium tetrafluoroborate, 100% nitric acid/trifluoroacetic anhydride, 100% nitric acid/concentrated sulfuric acid, fuming nitric acid, 100% nitric acid/acetic anhydride, fuming nitric acid/concentrated sulfuric acid, fuming nitric acid/acetic anhydride, fuming nitric acid/trifluoroacetic anhydride, fuming nitric acid/acetic anhydride, sulfur trioxide/nitric acid, phosphorus pentoxide/nitric acid, fuming sulfuric acid/fuming nitric acid, and fuming sulfuric acid/100% nitric acid. when the nitration system used is 100% nitric acid, 100% nitric acid/acetic anhydride, 100% nitric acid/trifluoroacetic anhydride, nitric acid/acetic anhydride, 100% nitric acid/concentrated sulfuric acid, fuming nitric acid, fuming nitric acid/concentrated sulfuric acid, fuming nitric acid/acetic anhydride, fuming nitric acid/trifluoroacetic anhydride, dinitrogen pentoxide, sulfur trioxide/nitric acid, phosphorus pentoxide/nitric acid, fuming sulfuric acid/fuming nitric acid, and fuming sulfuric acid/100% nitric acid, the ratio of the mass of 3-amino-4-[1H-tetrazolyl]-1H-pyrazole to the volume of nitration system is 1 g:(5-50) mL. when the nitration system used is nitronium tetrafluoroborate, the mole ratio of 3-amino-4-[1H-tetrazolyl]-1H-pyrazole to nitronium tetrafluoroborate 1:(1-50). Preferably, the reaction temperature in step 2 is −20° C. to 130° C., and the reaction time in step 2 is 0.5 hour to 48 hours.

The present invention further discloses an application of the compound as recited above, or the compound prepared by using the precursor as recited above, or the compound prepared by the preparation method as recited above, in the field of explosives, and the explosive including the same. Wherein preferably, the explosive is a primer. Preferably, the explosive is a green environmentally-friendly primer. Preferably, the explosive is a metal-free primer.

The compounds, preparation methods and applications of the invention may bring about the following beneficial effects:

1. The compounds may be obtained by simple preparation methods, and simple reaction steps and conditions.
2. There is no pollution during the reaction process and during use.
3. The compounds are no metal needed in the structure, and are green and reliable.
4. The compound has good stability, and high impact sensitivity and friction sensitivity.
5. The compound has high initiation capability and appropriate minimum initiating charge.

Figure 1:
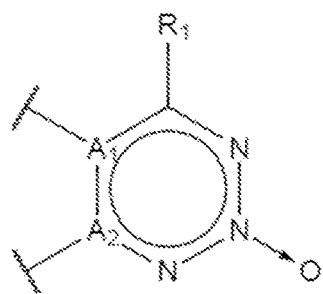
FIG. 1 is a chemical structure diagram showing a partial structure of a compound of the present invention.

Here, the reference numerals of FIGS. 1-30 are explained as follows:

$A_1$ to $A_{11}$: atoms; I, II, III: compounds; 1: an electric ignition head; 2: a sample; 3: a lead plate; 4: a power supply; 5: a switch

DETAILED DESCRIPTION OF THE INVENTION

To further explain the technical means and efficacy of the present invention in order to achieve the intended purpose of the invention, the specific embodiments, structures, features and functions of the present invention are described in detail below with reference to the accompanying drawings and preferred embodiments.

FIG. 1 is a chemical structure diagram showing a partial structure of a compound of the present invention. It may be seen that this structure includes at least a structure including three nitrogen atoms connected each other, with the middle nitrogen atom being bonded to an oxygen atom by a nitrogen-oxygen coordinate bond.

A compound comprising the structure shown in the FIG. 1 may have the advantages of strong initiation force, good stability and the like. On the other hand, the structure is only composed of non-metal atoms such as carbon, nitrogen, oxygen, hydrogen . . . and the like and does not contain metal, so that a compound without metal and is used as an explosive and a primer may be manufactured, and therefore green and environment-friendly explosives and primer may be prepared.

Further, a variety of different compounds may be derived from the structures shown in FIG. 1. Since these compounds all have the structure shown in FIG. 1, they all have the technical effects described above.

For example, In an embodiment, among the structures shown in FIG. 1, the atoms $A_1$ and $A_2$ are carbon atoms. In such an embodiment, at least a structure of 2-oxo-1,2,3-triazine is included. However, it is worth noting that the atoms $A_1$ and $A_2$ are not limited to carbon atoms in the structures shown in FIG. 1. In an embodiment, the atoms $A_1$ and $A_2$ may be selected from one or more of a carbon atom, a nitrogen atom, an oxygen atom, a phosphorus atom, and a sulfur atom. For example, the atoms $A_1$ and $A_2$ may be selected from one or more of a carbon atom and a nitrogen atom. In an embodiment, the atoms $A_1$ and $A_2$ may be carbon atoms and nitrogen atoms, respectively. In an embodiment, atom $A_1$ is a carbon atom and atom $A_2$ is a nitrogen atom.

In another aspect, for example, in the positions 5 and 6 (the upper left and lower left positions of the heterocyclic ring shown in FIG. 1, i.e. the positions of atoms $A_1$ and $A_2$) of the structure shown in FIG. 1, other bonds may be formed to form a ring to form a fused ring (ring fused) compound, i.e., a polycyclic compound fused together. For example, the fused ring compound may be a bicyclic ring compound, a tricyclic ring compound or even larger polycyclic compounds.

These one or more rings fused with the structure shown in FIG. 1 may be a three-membered ring, a four-membered ring, a five-membered ring, a six-membered ring, a seven-membered ring, an eight-membered ring, or a multiple-membered ring with more members. For example, a five-membered ring may be fused to the structure shown in FIG. 1, sharing two atoms at positions 5 and 6 of the structure shown in FIG. 1, for example sharing two carbon atoms. Alternatively, a six-membered ring may be fused to the structure shown in FIG. 1, sharing two atoms at positions 5 and 6 of the structure shown in FIG. 1, for example sharing two carbon atoms. Alternatively, a fused ring, which is composed of a five-membered ring and a six-membered ring, is fused to the structure shown in FIG. 1, sharing two atoms at positions 5 and 6 of the structure shown in FIG. 1, for example, sharing two carbon atoms.

These one or more monocyclic rings fused to the structure shown in FIG. 1 may be composed entirely of carbon atoms, for example, may be a benzene ring; however, they may also include one, two, three or more heteroatoms, even all of them. These heteroatoms may include a boron atom, a nitrogen atom, an oxygen atom, a silicon atom, a phosphorus atom, a sulfur atom, an arsenic atom, a selenium atom, a tellurium atom, and any other atoms with reasonable chemical structures in the periodic table. The types of atoms contained in the same ring may be one (the entire ring is composed of the same atom), two, three or more, or the atomic species being different throughout the ring.

In addition to the atoms shared with the structure shown in FIG. 1, the atoms in other portions in these rings may be single-bonded or double-bonded, or even triple-bonded to each other; which may be bonded by a plurality of conjugated single-double bonds to form aromatic rings. Specifically, the rings may be aromatic heterocycles such as furan, pyrrole, thiophene, imidazole, pyrazole, oxazole, thiazole, pyridine, pyrazine, pyrimidine, pyridazine, furazan, or other triazoles, tetrazoles, triazines, tetrazines, etc. For example, the aromatic ring fused to the structure shown in FIG. 1 may be pyrazole, wherein the two carbon atoms at positions 4 and 5 therein are at the positions 5 and 6 of the structure shown in FIG. 1, respectively. Alternatively, the aromatic ring fused to the structure shown in FIG. 1 may be furazan, wherein the two carbon atoms at the positions 2 and 3 therein are at the positions 5 and 6 of the structure shown in FIG. 1, respectively. Alternatively, the aromatic ring fused to the structure shown in FIG. 1 may be pyridazine, wherein the two carbon atoms at the positions 4 and 5 therein are at the positions 5 and 6 of the structure shown in FIG. 1, respectively. Alternatively, the aromatic ring fused to the structure shown in FIG. 1 may be pyrimidine, wherein the two carbon atoms at the positions 4 and 5 therein are at the positions 5 and 6 of the structure shown in FIG. 1, respectively. Alternatively, the aromatic ring fused to the structure shown in FIG. 1 may be pyrazine, wherein the two carbon atoms at the positions 2 and 3 therein are at the positions 5 and 6 of the structure shown in FIG. 1, respectively.

And these one or more monocyclic rings fused to the structure shown in FIG. 1 may have no substituent or have one or more substituents. These substituents may be: (1) saturated hydrocarbon groups such as an alkane group or the like; (2) functionalized saturated hydrocarbon groups such as a nitroalkane group, a gem-dinitroalkane group, a nitroform alkane group, a halogenated alkane group or the like; (3) an alcohol group; (4) an ether group and a thioether group; (5) a carboxylic group, an ester group, a nitrate group, a sulfonic acid group, a sulfonate group, etc.; (6) a ketone group, an amide group, and a hydrazide group; (7) an aldehyde group; (8) unsaturated aliphatic hydrocarbon groups such as an olefin group, an alkyne group, a halogenated alkene group, a nitroalkyne group, etc.; (9) unsaturated aromatic hydrocarbon groups such as a monocyclic aromatic hydrocarbon group, a polycyclic aromatic hydrocarbon group, a fused ring aromatic hydrocarbon group and a functionalized monocyclic aromatic hydrocarbon group, a functionalized polycyclic aromatic hydrocarbon group, and a functionalized fused ring aromatic hydrocarbon group; (10) heterocyclic aromatic hydrocarbon groups such as thiophene, pyridine, furan, azole ring, azine ring, oxazole ring and the like and corresponding monofunctional or polyfunctional groups; (11) heterocyclic non-aromatic hydrocarbon groups such as an aza-bridged hydrocarbon group, an oxa-bridged hydrocarbon group, etc. (12) halogen atoms; (13) a cyano group, and an oximido group; (14) an amino group, an imino group, an azo group, an azoxy group, an azido group, and a hydrazine group; (15) a hydroxyl group, a hydroxylamine group, an alkoxy group; (16) a nitro group and a nitroso group. For example, it may be a nitro group, more specifically a nitro group on the carbon in position 5 of the pyrazole. Alternatively, the atoms on one or more of the monocyclic rings fused to the structure shown in FIG. 1 may also form a coordinate bond with the substituent. For example, it may be that the nitrogen atom thereon forms a coordinate bond with the substituent oxygen atom. Specifically, it may be the nitrogen atom on the furazan forms a coordinate bond with the substituent oxygen atom.

Figure 2:
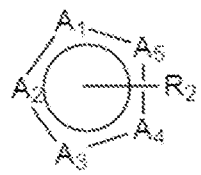
FIG. 2 is a chemical structural diagram showing a partial structure of one type of embodiment of a compound of the present invention.

In the structure shown in FIG. 1, a substituent, which is indicated as $R_1$ in FIG. 1, is located at the position 4 (upper position of the heterocyclic ring in FIG. 1). Specifically, $R_1$ may be hydrogen, amino group, nitro group, nitroamino group, azido group, fluorine, chlorine, bromine, iodine, $C_nH_m(NO_2)_p$ group (wherein m+p=2n+1), or group as shown in FIG. 2. In the structure shown in FIG. 2, the atoms such as $A_1$ to $A_5$ may be carbon atoms, nitrogen atoms, oxygen atoms, phosphorus atoms or sulfur atoms, and may be the same or different kinds of. In the structure shown in FIG. 2, the number of substituents on the atoms such as $A_1$ to $A_5$ may be 0, 1, 2, 3, 4 or 5. A substituent $R_2$ may be included in the structure shown in FIG. 2. The substituent $R_2$ may be hydrogen, amino group, nitro group, nitroamino group, azido group, fluorine, chlorine, bromine, iodine, $C_nH_m(NO_2)_p$ group, or the structure shown in FIG. 2.

Figure 5:
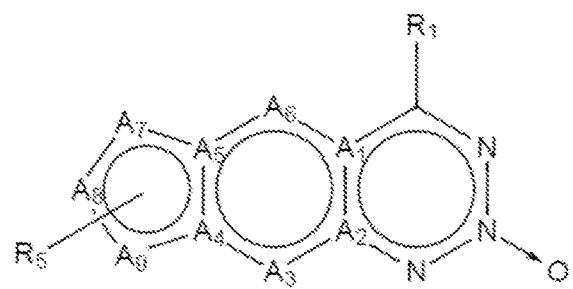
FIGS. 3-5 are chemical structural diagrams showing one type of embodiment of a compound of the present invention.
Figure 3:
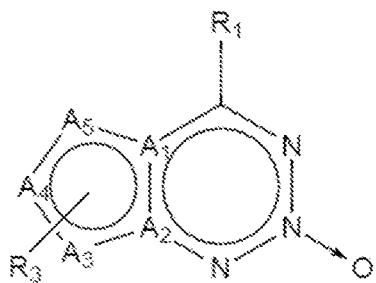
Figure 4:
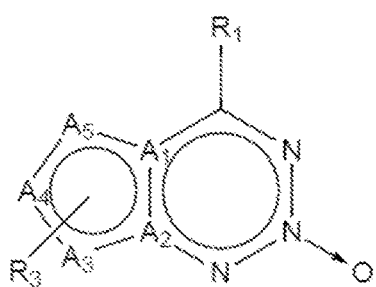

Specifically, the compound of the formula shown in FIG. 1 may specifically be, for example, the compounds of the formula shown in FIGS. 3, 4, and 5.

FIG. 3 is a chemical structural diagram of one type of embodiment of a compound of the present invention. Referring to FIG. 3, the structure shown in FIG. 1 is fused to a five-membered ring having at least one substituent $R_3$. In the structure shown in FIG. 3, the atoms such as $A_1$ to $A_5$ may be carbon atoms, nitrogen atoms, oxygen atoms, phosphorus atoms or sulfur atoms, and may be the same or different. In the structure shown in FIG. 3, the number of substituents on atoms such as $A_1$ to $A_5$ may be 0, 1, 2, 3, 4 or 5. In the structure shown in FIG. 3, the substituent $R_3$ may be hydrogen, amino group, nitro group, nitroamino group, azido group, fluorine, chlorine, bromine, iodine, $C_nH_m(NO_2)_p$ group (wherein m+p=2n+1), or the structure shown in FIG. 2. The substituent $R_3$ may be one, or a plurality of the same or different ones.

FIG. 4 is a chemical structural diagram of another type of embodiment of a compound of the present invention. Referring to FIG. 4, the structure shown in FIG. 1 is fused to a six-membered ring having at least one substituent $R_4$. In the structure shown in FIG. 4, the atoms such as $A_1$ to $A_6$ may be carbon atoms, nitrogen atoms, oxygen atoms, phosphorus atoms or sulfur atoms, and may be the same or different. In the structure shown in FIG. 4, the number of substituents on atoms such as $A_1$ to $A_6$ may be 0, 1, 2, 3, 4, 5 or 6. In the structure shown in FIG. 4, the substituent $R_4$ may be hydrogen, amino group, nitro group, nitroamino group, azido group, fluorine, chlorine, bromine, iodine, $C_nH_m(NO_2)_p$ group (wherein m+p=2n+1), or the structure shown in FIG. 2. The substituent $R_4$ may be one, or a plurality of the same or different ones.

FIG. 5 is a chemical structural diagram of yet another type of embodiment of a compound of the present invention. Referring to FIG. 5, the structure shown in FIG. 1 is fused to a six-membered ring which is in turn fused to with a five-membered ring having at least one substituent $R_5$. In the structure shown in FIG. 5, the atoms such as $A_1$ to $A_9$ may be carbon atoms, nitrogen atoms, oxygen atoms, phosphorus atoms or sulfur atoms, and may be the same or different. In the structure shown in FIG. 5, the number of substituents on atoms such as $A_4$ to $A_5$, and $A_7$ to $A_9$ may be 0, 1, 2, 3, 4, 5 or 6. In the structure shown in FIG. 5, the substituent $R_5$ may be hydrogen, amino group, nitro group, nitroamino group, azido group, fluorine, chlorine, bromine, iodine, $C_nH_m(NO_2)_p$ group (wherein m+p=2n+1), or the structure shown in FIG. 2. The substituent $R_5$ may be one, or a plurality of the same or different ones.

The structures shown in FIGS. 3 to 5 above and the compounds derived therefrom have different properties, but all have similar structures, so they all have the technical effects of strong initiation force, good stability, and the like as described in the present application.

On the other hand, as shown in the structure shown in FIG. 1, the general synthesis method may be as follows:

[Step 1]

Figure 6:
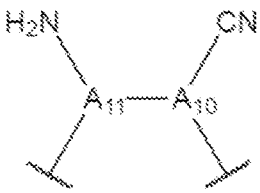
FIG. 6 is a chemical structural diagram showing a partial structure of a precursor in a method for synthesizing a compound of the present invention.

The precursor material, i.e. the structure including the formula shown in FIG. 6, is synthesized.

Specifically, the precursor with the structure of the formula shown in FIG. 6 to be synthesized herein, may include two atoms $A_{10}$ and $A_{11}$, wherein $A_{10}$ may be bonded to at least one cyano group, and $A_{11}$ may be bonded to at least one amino group. In the next tetrazole ring-closing reaction, these cyano groups and amino groups participate in the reaction such that the two atoms $A_{10}$ and Au become, for example, $A_1$ and $A_2$ in the structure shown in FIG. 1, or become, for example, two of $A_1$ to $A_6$ in the structures shown in FIG. 3 to FIG. 5.

In an embodiment, the atoms such as $A_{10}$ and $A_{11}$ may be a carbon atom, a nitrogen atom, an oxygen atom, a phosphorus atom or a sulfur atom, and may be the same or different. In an embodiment, the atoms $A_{10}$ and $A_{11}$ are carbon atoms. The atoms $A_{10}$ and $A_{11}$ are respectively a carbon atom and a nitrogen atom.

In an embodiment, the precursor material comprises a polycyclic ring. In an embodiment, $A_{10}$ and $A_{11}$ are part of a polycyclic ring. The polycyclic ring here may be a three-membered ring, a four-membered ring, a five-membered ring, a six-membered ring, a seven-membered ring, an eight-membered ring or even a multi-membered ring. For example, it may be a five-membered ring or a six-membered ring. Or, it may be a fused ring of a five-membered ring and a six-membered ring. In an embodiment, the precursor material comprises an aromatic ring. In an embodiment, $A_{10}$ and $A_{11}$ are part of the aromatic ring. In another embodiment, the precursor material comprises a polycyclic ring, but atoms such as $A_{10}$ and $A_{11}$ are not part of the polycyclic ring.

These rings may all consist of carbon atoms, for example, may be a benzene ring; but may also include one, two, three or more heteroatoms, or even all of them. These heteroatoms may include a boron atom, a nitrogen atom, an oxygen atom, a silicon atom, a phosphorus atom, a sulfur atom, an arsenic atom, a selenium atom, a tellurium atom, and the like, and other atoms with reasonable chemical structures in the periodic table. The types of atoms contained in the same ring may be one (the entire ring is composed of the same atom), two, three or more, and even the atomic species on the entire ring are different.

These rings may be aromatic heterocycles such as furan, pyrrole, thiophene, imidazole, pyrazole, oxazole, thiazole, pyridine, pyrazine, pyrimidine, pyridazine, furazan, or other triazoles, tetrazoles, triazines, tetrazines, etc.

These rings may have no substituents or have one or more substituents. These substituents may be:

(1) saturated hydrocarbon groups such as an alkane group or the like; (2) functionalized saturated hydrocarbon groups such as a nitroalkane group, a gem-dinitroalkane group, a nitroform alkane group, a halogenated alkane group or the like; (3) an alcohol group; (4) an ether group and a thioether group; (5) a carboxylic acid group, an ester group, a nitrate group, a sulfonic acid group, a sulfonate group, etc.; (6) a ketone group, an amide group, and a hydrazide group; (7) an aldehyde group; (8) unsaturated aliphatic hydrocarbon groups such as an olefin group, an alkyne group, a halogenated alkene group, a nitroalkyne group, etc.; (9) unsaturated aromatic hydrocarbon groups such as a monocyclic aromatic hydrocarbon group, a polycyclic aromatic hydrocarbon group, a fused ring aromatic hydrocarbon group and a functionalized monocyclic aromatic hydrocarbon group, a functionalized polycyclic aromatic hydrocarbon group, and a functionalized fused ring aromatic hydrocarbon group; (10) heterocyclic aromatic hydrocarbon groups such as thiophene, pyridine, furan, azole ring, azine ring, oxazole ring and the like and corresponding monofunctional or polyfunctional groups; (11) heterocyclic non-aromatic hydrocarbon groups such as an aza-bridged hydrocarbon group, an oxa-bridged hydrocarbon group, etc. (12) halogen atoms; (13) a cyano group, and an oximido group; (14) an amino group, an imino group, an azo group, an azoxy group, an azido group, and a hydrazine group; (15) a hydroxyl group, a hydroxylamine group, an alkoxy group; (16) a nitro group, a nitroso group, or a combination of these functional groups. In an embodiment, these substituents may be structures in which atoms such as $A_{10}$ and $A_{11}$ are located.

In step 1, different precursor materials to be synthesized, different synthesis methods and different synthesis conditions can be selected according to the products to be synthesized. However, if the precursor of the desired product can be directly obtained, this step is skipped.

[Step 2]

A tetrazole ring-closing reaction is performed on the precursor, and a first intermediate is obtained.

Specifically, the steps are as follows:

(1) Dispersing the precursor in a solvent.

(2) Adding a certain amount of salts and a certain amount of azides, and reacting for a certain time at a certain reaction temperature.

(3) Adding an acid, and purifying to obtain a first intermediate.

The solvent in the step (1) may be any one solvent of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, etc.; or a mixture of suitable two and more solvents thereof, for example a mixed solution of, water, ethanol, dimethyl sulfoxide, N,N-dimethylformamide or acetone, and methanol, in a volume ratio of 4:1. However, the present invention is not limited thereto, and it should be considered that any solvent suitable for the reaction can be employed in the present invention.

The reaction temperature in step 2 (2) may be −20° C. to 130° C., for example, 70° C. to 120° C., for example, 70° C., 110° C., or 120° C. However, the present invention is not limited thereto, and it should be considered that any reaction temperature suitable for the reaction can be employed in the present invention.

The reaction time in step 2 (2) may be from 2 hours to 24 hours, for example from 2 hours to 10 hours, for example from 2 hours to 8 hours, for example, may be 2 hours, 3 hours, 4 hours, 5 hours, 7 hours, 10 hours, or 24 hours. However, the present invention is not limited thereto, and it should be considered that any reaction time suitable for the reaction can be employed in the present invention.

In step 2 (2), the mole ratio of salts to be added may be the salts:the precursor=1:1 to 6:1, for example, may be 20:9 to 50:9, for example, may be 1:1, 20:9, 40:9, 50:9, or any other suitable ratio. The salts here may, for example, have the general formula $M_aX_b$, wherein: M may be Fe, Co, Ni, Mn, Zn, Cd, Au, Ag, Cu, Cr, Al, V, $NH_4$, $(CH_3)_2NH_2$, $(CH_3)_3NH$, $(CH_3CH_2)_2NH_2$, $(CH_3CH_2)_3NH$, etc., and X may be F, Cl, Br, I, $NO_3$, $SO_4$, $HSO_4$, $CO_3$, $HCO_3$, HCOO, $CH_3COO$, $CF_3COO$, $(COO)_2$, $CH_2(COO)_2$, etc. For example, M may be $NH_4$, Al, $(CH_3CH_2)_3NH$, Co, etc., X may be F, Cl, etc., and the corresponding a and b are selected. For example, the salts herein may be ammonium fluoride, ammonium chloride, ammonium nitrate, cobaltous chloride, dimethylamine hydrochloride or the like. However, the present invention is not limited thereto, and it should be considered that any salts suitable for the reaction can be employed in the present invention.

In step 2 (2), the molar ratio of azides added may be the azides:precursor=1:1 to 6:1. The azides used may be represented by the general formula $R_a(N_3)_b$, wherein R may be Li, Na, K, Rb, Cu, Fe, Ag, Au, Pb, Cd, Ni, H, $NH_4$, etc., and the corresponding a and b are selected. For example, the azides here may be sodium azide, ammonium azide or the like. However, the present invention is not limited thereto, and it should be considered that any azides suitable for the present reaction can be employed in the present invention.

In step 2 (3), the acids to be added may be: nitric acid, sulfuric acid, hydrochloric acid, hydrobromic acid, hydrofluoric acid, hydroiodic acid, formic acid, acetic acid, acetic anhydride, oxalic acid, malonic acid, trifluoroacetic acid or the like; it is possible to use a single acid as described above or a mixture of two or more acids. For example, it may be hydrochloric acid, formic acid, acetic anhydride, or trifluoroacetic acid; however, the present invention is not limited thereto, and it should be considered that any acids suitable for the reaction can be employed in the present invention.

In step 2 (3), the amount of the acid to be added may be adjusted to adjust the pH of the solution to 1.0 to 4.0, for example, may be 1.0 to 3.5, for example, may be 2.0 to 3.0, for example, 1.4, 2.0, 2.4, 2.5. 3.0, 3.1, 3.3, etc.; however, the invention is not limited thereto, and it should be considered as the amount of acid added to adjust the solution to any desired pH.

[Step 3]

A rearrangement reaction is performed on the first intermediate obtained in step 2, and a reaction is performed at the position corresponding to $R_1$ moiety in the structure shown in FIG. 1 to produce an azido group (—N3) to obtain a product (when the group of the product to be synthesized corresponding to $R_1$ moiety in the structure shown in FIG. 1 being an azido group) or a second intermediate (when the group of the product to be synthesized corresponding to $R_1$ moiety in the structure shown in FIG. 1 being not an azido group).

Specifically, the steps are as follows:

(1) Adding the first intermediate to a nitration system, controlling the temperature of the reaction system after the addition, and maintaining the nitration reaction for a certain period of time at a certain temperature.

(2) Terminating the reaction, followed by filtration and purification to obtain a product or a second intermediate.

In step 3 (1), the reaction temperature may be from −20° C. to 130° C., for example from −20° C. to 110° C., for example from −20° C. to 100° C., for example −20° C. to room temperature, for example, −20° C., −10° C., −5° C., 0° C., 4° C. or room temperature, or may also be, for example, 40° C. to 80° C., for example 50° C. to 70° C., for example 50° C., or for example 60° C. However, the present invention is not limited thereto, and it should be considered that any reaction temperature suitable for the reaction can be employed in the present invention.

In step 3 (1), the reaction time may be from 0.5 hour to 48 hours, for example from 0.5 hour to 12 hours, for example from 0.5 hour to 4 hours, for example, 0.5 hour, 1 hour, 2 hours, 3 hours, 4 hours, or may be 7 hours. However, the present invention is not limited thereto, and it should be considered that any reaction time suitable for the reaction can be employed in the present invention.

In step 3 (1), the nitration system may be commercially available fuming nitric acid or 100% nitric acid, or may be other nitration systems such as dinitrogen pentoxide, nitronium tetrafluoroborate, 100% nitric acid/trifluoroacetic anhydride, 100% nitric acid/concentrated sulfuric acid, fuming nitric acid, 100% nitric acid/acetic anhydride, fuming nitric acid/concentrated sulfuric acid, fuming nitric acid/acetic anhydride, fuming nitric acid/trifluoroacetic anhydride, fuming nitric acid/acetic anhydride, sulfur trioxide/nitric acid, phosphorus pentoxide/nitric acid, fuming sulfuric acid/fuming nitric acid, fuming sulfuric acid/100% nitric acid, and the like.

When the nitration system used is 100% nitric acid, 100% nitric acid/acetic anhydride, 100% nitric acid/trifluoroacetic anhydride, nitric acid/acetic anhydride, 100% nitric acid/concentrated sulfuric acid, fuming nitric acid, fuming nitric acid/concentrated sulfuric acid, fuming nitric acid/acetic anhydride, fuming nitric acid/trifluoroacetic anhydride, dinitrogen pentoxide, sulfur trioxide/nitric acid, phosphorus pentoxide/nitric acid, fuming sulfuric acid/fuming nitric acid, fuming sulfuric acid/100% nitric acid, etc, the ratio of the mass of first intermediate to the volume of nitration system may be 1 g:5 mL to 1 g:50 mL; the ratio of the components of the nitration system may be, for example, a volume ratio of 1:1 to 3:1, for example, a volume ratio of 1:1. For example, 100% nitric acid/trifluoroacetic anhydride in a volume ratio of 1:1 or 100% nitric acid/concentrated sulfuric acid in a volume ratio of 1:1 may be used as the nitration system.

When the nitration system used is nitronium tetrafluoroborate, the molar ratio of the first intermediate to the nitronium tetrafluoroborate may be from 1:1 to 1:50; the solvent used may not react with the nitration system or the first intermediate and the second intermediate, for example, may be acetonitrile.

In step 3 (1), the specific method for terminating the reaction may be, for example, pouring the reaction system into ice or ice water so that the nitration system is diluted and cooled, the reaction is stopped, and the product is precipitated.

[Step 4]

In the product to be synthesized, if the group corresponding $R_1$ moiety in the structure shown in FIG. 1 is not an azido group, a substituent displacement reaction is carried out.

When the group of $R_1$ moiety is chlorine, amino, nitro or nitroamino, the corresponding reaction steps are as follows:

[A. $R_1$ moiety being chlorine (—Cl)]

(1) Dispersing the second intermediate in a solvent.

(2) Introducing chlorine gas flow and reacting for a certain period of time at a certain temperature.

(3) Performing filtration and purification to obtain the final product.

In step 4 A (1), the solvent used may be various common organic solvents, except those reacted with the second intermediate or chlorine gas thus the subsequent reaction cannot be carried out. For example, in step 4 (1), the solvent used may be dichloromethane.

In step 4 A (2), the flow rate of the chlorine gas flow may be between 1 mL and 5 mL per minute, for example, 2 mL to 5 mL per minute, for example, 3 mL to 4 mL per minute, or for example 5 mL per minute.

In step 4 A (2), the reaction temperature may be from 30° C. to 100° C., for example from 50° C. to 90° C., for example from 60° C. to 70° C., for example 60° C., or for example 70° C.

In step 4A (2), the reaction time may be, for example, from 1 hour to 10 hours, for example, from 1 hour to 5 hours, for example, from 1 hour to 3 hours, for example, 1 hour, or for example, 2 hours.

[B. $R_1$ moiety being amino (—NH$_2$)]

(1) Dispersing the second intermediate in a solvent.

(2) Adding a certain amount of strong ammonia solution, performing reflux reaction for a period of time, and then cooling after the reaction.

(3) Performing filtration and purification to obtain the final product.

In the step 4 B (1), the solvent used may be various common organic solvents, except those reacted with the second intermediate or strong ammonia solution thus the subsequent reaction cannot be carried out. For example, in the step 4B (1), the solvent used may be methanol.

In the step 4 B (2), the concentration of the strong ammonia solution may be, for example, 10% to 32%.

In the step 4 B (2), the ratio of the mass of second intermediate to the volume of strong ammonia solution may be, for example, 1 g:1 mL to 1 g:100 mL, for example, may be 1 g:5 mL to 1 g:20 mL, for example, may be 1 g:6 mL to 1 g:12 mL.

In the step 4 B (2), the time for reflux reaction is, for example, 0.5 hour to 24 hours, for example, 1 hour to 12 hours, for example, 2 hours to 8 hours, for example, 2 hours, or for example, 4 hours.

[C. $R_1$ moiety being nitro (—NO$_2$)]

(1) Dispersing the second intermediate in a solvent.

(2) Adding a certain amount of strong ammonia solution, performing reflux reaction for a period of time, and cooling and filtering to obtain a solid.

(3) Adding this solid to the oxidizing solution and reacting for a while.

(4) Terminating the reaction and purifying to give the final product.

In the step 4 C (1), the solvent used may be various common organic solvents, except those may react with the second intermediate or strong ammonia solution thus the subsequent reaction cannot be carried out. For example, in the step 4 C (1), the solvent used may be methanol.

In the step 4 C (2), the concentration of the strong ammonia solution may be, for example, 10% to 32%.

In the step 4 C (2), the ratio of the mass of second intermediate to the volume of strong ammonia solution may be, for example, 1 g:1 mL to 1 g:100 mL, for example, may be 1 g:5 mL to 1 g:20 mL, for example, may be 1 g:6 mL to 1 g:12 mL.

In the step 4 C (2), the time for reflux reaction is, for example, from 0.5 hour to 24 hours, for example, from 1 hour to 12 hours, for example, from 2 hours to 8 hours, for example, 2 hours, or for example, 4 hours.

In the step 4 C (3), the oxidizing solution may be: a mixed solution of concentrated sulfuric acid and 30% hydrogen peroxide, a mixed solution of concentrated sulfuric acid and 50% hydrogen peroxide, a mixed solution of concentrated sulfuric acid and trifluoroacetic acid, a mixed solution of concentrated sulfuric acid and peroxyacetic acid, or a mixed solution of concentrated sulfuric acid and acetic anhydride. The volume ratio of each component in the oxidizing solution may be, for example, 1:1, for example, a mixed solution of concentrated sulfuric acid and 30% hydrogen peroxide in a volume ratio of 1:1.

The reaction time in the step 4 C (3) may be, for example, 0.5 hour to 12 hours, for example, 0.5 hour to 4 hours, for example, 0.5 hour, 1 hour, 2 hours, or 4 hours.

[D. $R_1$ moiety being nitramino (—NHNO$_2$)]

(1) Dispersing the second intermediate in a solvent.

(2) Adding a certain amount of strong ammonia solution, and performing reflux reaction for a period of time.

(3) Cooling and filtering to obtain a solid.

(4) Adding the obtained solid to the nitration system for a certain period of time.

(5) Terminating the reaction, filtering, and purifying to give the final product.

In the step 4 D (1), the solvent used may be various common organic solvents, except those reacted with the second intermediate or strong ammonia solution thus the subsequent reaction cannot be carried out. For example, in the step 4 D (1), the solvent used may be methanol.

In the step 4 D (2), the concentration of strong ammonia solution may be, for example, 10% to 32%.

In the step 4 D (2), the ratio of the mass of second intermediate to the volume of strong ammonia solution may be, for example, 1 g:1 mL to 1 g:100 mL, for example, may be 1 g:5 mL to 1 g:20 mL, may be, for example, 1 g:6 mL to 1 g:12 mL.

In the step 4 D (2), the time for reflux reaction is, for example, from 0.5 hour to 24 hours, for example, from 1 hour to 12 hours, for example, from 2 hours to 8 hours, for example, 2 hours, or for example, 4 hours.

The reaction temperature in the step 4 D (4) may be from −20° C. to 130° C., for example from −20° C. to 110° C., for example from −20° C. to 100° C., for example −20° C. to room temperature, for example, −20° C., 10° C., 4° C. or room temperature. However, the present invention is not limited thereto, and it should be considered that any reaction temperature suitable for the reaction can be employed in the present invention.

The reaction time in the step 4 D (4) may be from 0.5 hour to 12 hours, for example from 0.5 hour to 4 hours, for example, 0.5 hour, 1 hour, 2 hours, or 4 hours. However, the present invention is not limited thereto, and it should be considered that any reaction time suitable for the reaction can be employed in the present invention.

In the step 4 D (4), the nitration system may be commercially available fuming nitric acid or 100% nitric acid, or may be other nitration systems such as dinitrogen pentoxide, nitronium tetrafluoroborate, 100% nitric acid/trifluoroacetic anhydride, 100% nitric acid/concentrated sulfuric acid, fuming nitric acid, 100% nitric acid/acetic anhydride, fuming nitric acid/concentrated sulfuric acid, fuming nitric acid/ acetic anhydride, fuming nitric acid/trifluoroacetic anhydride, fuming nitric acid/acetic anhydride, sulfur trioxide/nitric acid, phosphorus pentoxide/nitric acid, fuming sulfuric acid/fuming nitric acid, fuming sulfuric acid/100% nitric acid, and the like.

When the nitration system used is 100% nitric acid, 100% nitric acid/acetic anhydride, 100% nitric acid/trifluoroacetic anhydride, nitric acid/acetic anhydride, 100% nitric acid/concentrated sulfuric acid, fuming nitric acid, fuming nitric acid/concentrated sulfuric acid, fuming nitric acid/acetic anhydride, fuming nitric acid/trifluoroacetic anhydride, dinitrogen pentoxide, sulfur trioxide/nitric acid, phosphorus pentoxide/nitric acid, fuming sulfuric acid/fuming nitric acid, fuming sulfuric acid/100% nitric acid, etc., the ratio of the mass of compound solid obtained in step 4 D (3) to the volume of nitration system is 1 g:5 mL to 1 g:50 mL.

When the nitration system used is nitronium tetrafluoroborate, the molar ratio of the solid obtained in the step 4 D (3) to the nitronium tetrafluoroborate may be from 1:1 to 1:50.

The nitration system used in the step 4 D (4) may be the same nitration system as the step 3 or a different nitration system.

A specific method for terminating the reaction in the step 4 D (5) may be, for example, pouring the reaction system into ice or ice water so that the nitration system is diluted and cooled, the reaction is stopped, and the product is precipitated.

Based on the above various compound formulas and the above-mentioned general synthetic methods, a number of detailed examples are given here, and are described in detail as follows:

Example 1

Figure 7:
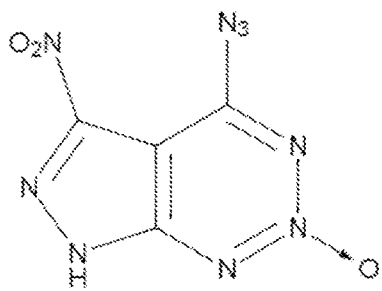
FIG. 7 is a chemical structural diagram of one embodiment of a compound of the present invention.
Figure 8:
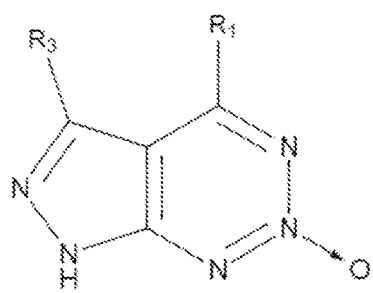
FIG. 8 is a chemical structural diagram showing a partial structure of one embodiment of a compound of the present invention.

FIG. 7 is a chemical structural diagram of one embodiment of a compound of the present invention. The compound shown in FIG. 7 has the specific name: 4-azido-5-nitro-7H-pyrazolo[3,4-d][1,2,3]triazine 2-oxide, having a structure as shown in FIG. 1, specifically having a structure as shown in FIG. 3, and more specifically having a structure as shown in FIG. 8.

The compound is a white to yellowish green powdery solid, and the pure material precipitated by recrystallization is white needle crystal, which has a crystal density of 1.5-1.9 g/cm$^3$; after dehydration at 70° C. to 90° C., the measured density is 1.6-2.0 g/cm$^3$ at room temperature. It has good dispersion and is not easy to adhere to glass containers. It has a thermal decomposition temperature of higher than 150° C., and it is not sensitive to light, water, steam, etc., with no obvious color change observed for a long time under direct sunlight. It is stable in nature and does not react with strong acids. By heating at 75° C. for 48 hours, it has a weight loss of 0.8%; it has a weight loss increased at 100° C., decomposition of about 2%, and apparent color changes. It does not react with copper, iron, etc. under environmental conditions, and does not react with plastic or paper.

[Synthetic Method]

Figure 9:
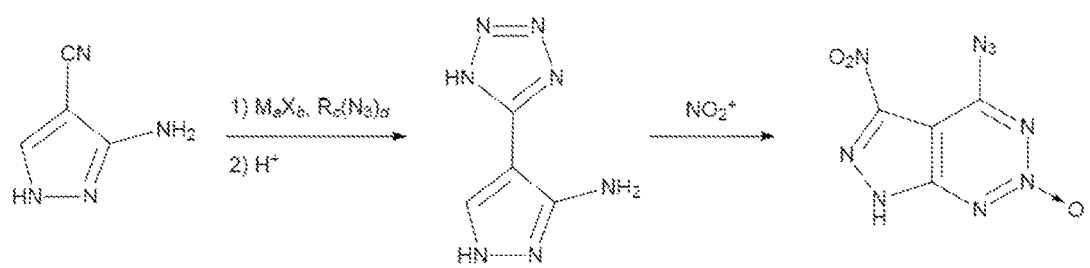
FIG. 9 is a chemical reaction formula of a specific synthesis method of the compound shown in FIG. 7.

The method for synthesizing the compound of Example 1 was carried out by using 3-amino-4-cyanopyrazole as a precursor. The specific reaction may be, for example, as shown in FIG. 9:

The first step reaction: synthesis of the first intermediate 3-amino-4-[1H-tetrazole]-1H-pyrazole (compound of formula II in FIG. 9) from the precursor 3-amino-4-cyanopyrazole (compound of formula I in FIG. 9)

The second step reaction: synthesis of the product 2-oxo-4-azido-5-nitro-7H-pyrazolo[3,4-d][1,2,3]triazine (compound of formula III in FIG. 9, which is the compound shown in FIG. 7) from the first intermediate 3-amino-4-[1H-tetrazolyl]-1H-pyrazole (compound of formula II)

The specific synthesis steps and reaction conditions are detailed here as follows:

The first step reaction: synthesis of the first intermediate 3-amino-4-[1H-tetrazole]-1H-pyrazole (compound of formula II in FIG. 9)

(1) The precursor 3-amino-4-[1H-tetrazole]-1H-pyrazole in Example 1, i.e., the compound of formula I in FIG. 9, was dispersed in a solvent at a certain temperature.

(2) Salts and azides were added to the reaction solution, and the reaction was carried out at a certain temperature.

(3) An acid was added to the reaction solution.

(4) Filtration and washing were performed, and the solid was dried to obtain the first intermediate of Example 1, i.e., the compound of formula II in FIG. 9.

In this part, the solvent used in the step (1), the salts and azides added to the step (2), the reaction temperature and reaction time, and the acid added in the step (3) can be referred to the reaction conditions described in the step 2 of the general synthesis method.

The second step reaction: synthesis of the product 2-oxo-4-azido-5-nitro-7H-pyrazolo[3,4-d][1,2,3]triazine (compound of formula III shown in FIG. 7)

(5) The first intermediate of Example 1, i.e., the compound of formula II in FIG. 9, was slowly added to a nitration system, and after the addition, the temperature of the reaction system was controlled, and the nitration reaction was maintained at a certain temperature for a certain period of time.

(6) The reaction was terminated, followed by filtration, washing and drying to give the product of Example 1, which is a compound of formula III in FIG. 9 (compound shown in FIG. 7).

In this part, the nitration system and reaction temperature in the step (5), and the manner of terminating the reaction in the step (6) can be referred to the reaction conditions described in the step 3 of the general synthesis method For specific examples of the above reaction, please refer to the following Examples 1A-1D.

Example 1A 1 g (9 mmol) of 3-amino-4-[1H-tetrazole]-1H-pyrazole was dispersed in 10 mL water at room temperature, then 0.48 g (9 mmol) of ammonium chloride and 0.59 g (9 mmol) of sodium azide were added in batches, then the reaction was carried out at 70° C. for 5 hours and cooled to room temperature; hydrochloric acid was added dropwise thereto until the pH of the solution was 2, followed by filtration, washing with 5 mL of ice water, and drying the solid to give 0.68 g of white powder with a yield of 50%.

Then, 0.3 g (2 mmol) of the obtained white powder was added into a 6 mL mixed solution of 100% nitric acid/trifluoroacetic anhydride in a volume ratio of 1:1, then the mixture was reacted at room temperature for 1 hour, the reaction liquid was poured into 50 g of ice water, followed by stirring for 0.5 hour, filtration, washing with 10 mL of ice water, and drying to give 0.31 g of a yellow powdery solid with a yield of 70%.

Example 1B 2 g (18 mmol) of 3-amino-4-[1H-tetrazole]-1H-pyrazole was dispersed in 70 mL of ethanol under ice-water bath, then 5.34 g (40 mmol) of aluminum chloride and 1.95 g (30 mmol) of sodium azide were added in batches, then the reaction was carried out at 120° C. for 2 hours, and cooled to room temperature; first acetic acid and then formic acid were added dropwise thereto until the pH of the solution was 3.3, followed by filtration, washing with 20 mL ice water, and drying the solid to give 2.20 g of white powder with a yield of 81%.

Then, 0.5 g (3.3 mmol) of the obtained white powder was added into a 20 mL mixed solution of 100% nitric acid/ trifluoroacetic anhydride in a volume ratio of 1:1, then the mixture was reacted at −10° C. for 4 hours; the reaction liquid was poured into 50 g of ice water, followed by stirring for 0.5 hour, filtration, washing with 20 mL of ice water, and drying to give 0.28 g of a yellow green powdery solid with a yield of 30%.

Example 1C 2 g (18 mmol) 3-amino-4-[1H-tetrazole]-1H-pyrazole was dispersed in 150 mL of dimethyl sulfoxide under ice-water bath, followed by the addition of 11 g (80 mmol) of triethylamine hydrochloride, and 6.5 g (100 mmol) of sodium azide in batches, then the mixture was reacted at 110° C. for 24 hours, then acetic anhydride was added dropwise until the pH of the solution was 2.5, followed by filtration, washing with 20 mL of ice water and then washing with 10 mL of diethyl ether, and drying the solid to give 0.81 g of white powder with a yield of 30%.

Then 0.5 g (3.3 mmol) of the obtained white powder was added to 20 mL of acetonitrile added with 1.1 g of nitronium tetrafluoroborate, then the mixture was reacted for 4 hours at 4° C., the reaction liquid was poured into 50 g of ice water, followed by stirring for 0.5 hour, filtration, washing with 20 mL of ice water, then washing with 10 mL of petroleum ether and drying to give 0.55 g of a white powdery solid with a yield of 75%.

Example 1D 2 g (18 mmol) 3-amino-4-[1H-tetrazole]-1H-pyrazole was dispersed into 800 mL of a solvent mixture of acetone and methanol in a volume ratio of 4:1 at room temperature, then, 13 g (100 mmol) of cobaltous chloride and 5.2 g (80 mmol) of sodium azide were added in batches, then the reaction was carried out under reflux for 10 hours, and then trifluoroacetic acid was added dropwise thereto until the pH of the solution was 1.4, followed by filtration, washing with 30 mL of ice water, then washing with 30 mL of diethyl ether, and drying the solid to give 2.26 g of white powder with a yield of 83%.

Then 0.5 g (3.3 mmol) of the obtained white powder was added to 30 mL of acetonitrile added with 0.9 g of nitrogen pentoxide, the reaction was carried out for 5 hours at −20° C., and the reaction solution was poured into 50 g of ice water, followed by stirring for 0.5 hour, filtering, washing with 20 mL of ice water, and drying the solid to give 0.58 g of a white powder solid with a yield of 79%.

[Measurement Results]

Figure 10:
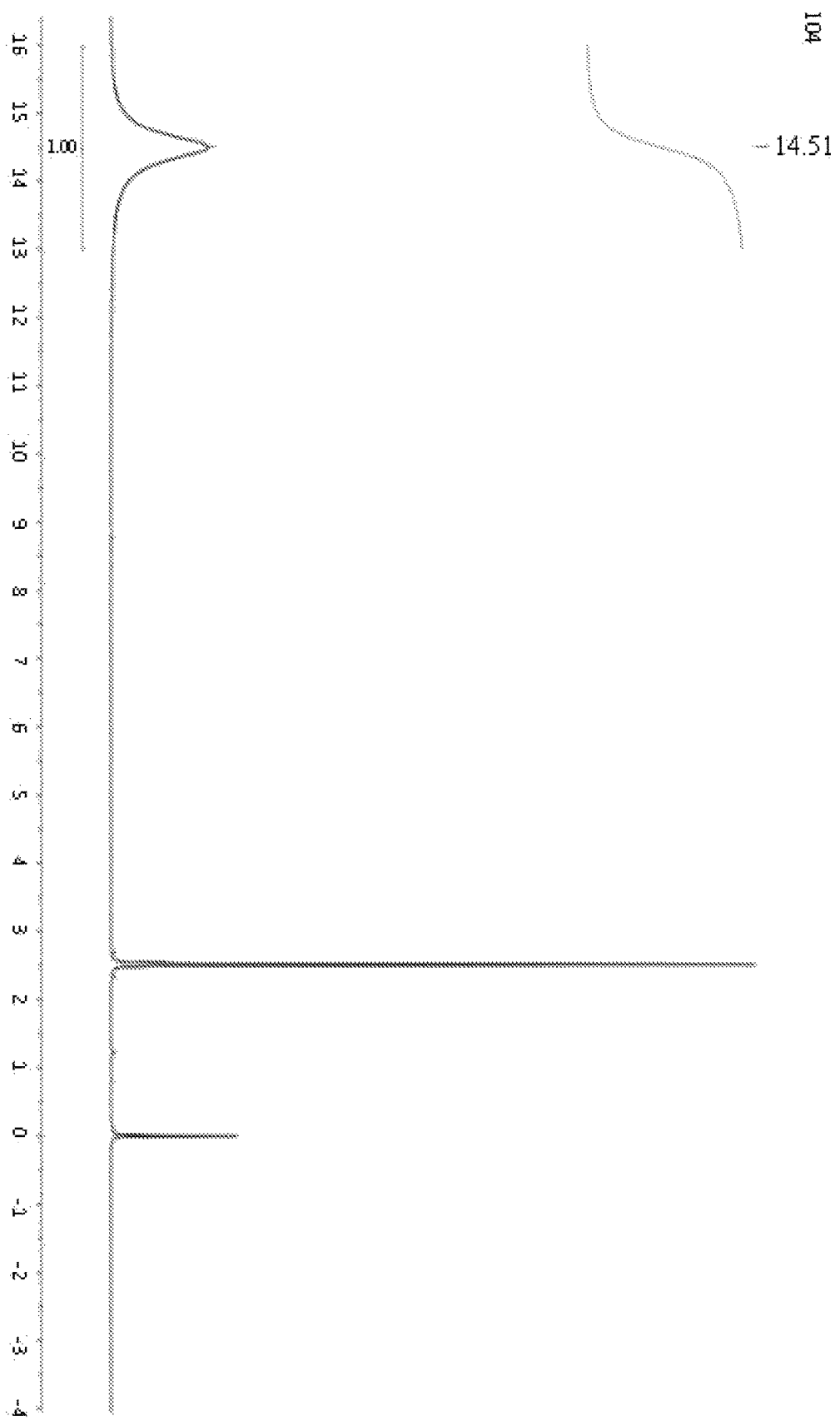
FIG. 10 is a $^1$H-NMR spectrum of the compound shown in FIG. 7.

The NMR spectra of the compound of formula III (i.e., the compound shown in FIG. 7) prepared in Examples 1A-1D is shown in FIG. 10, and the characteristic NMR spectra shift is: $^1$H NMR (400 MHz, DMSO-d$_6$, 25° C.) δ(ppm): 14.51 (brs, 1H, NH).

Figure 11:
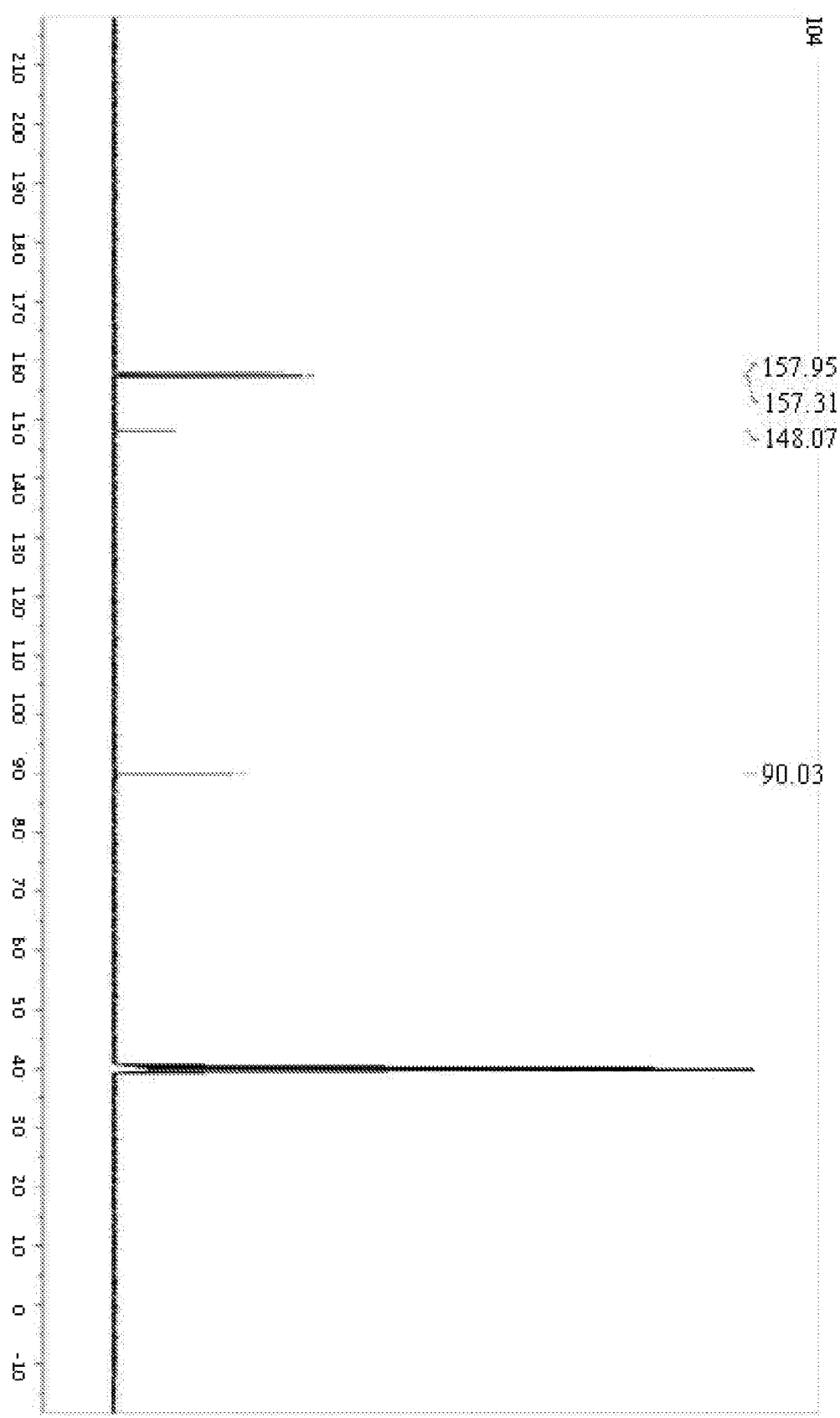
FIG. 11 is a $^{13}$C-NMR spectrum of the compound shown in FIG. 7.

The NMR spectra of the compound of formula III (i.e., the compound shown in FIG. 7) prepared in Examples 1A-1D is shown in FIG. 11, and the characteristic NMR spectra shift is: $^{13}$C NMR (100 MHz, DMSO-d$_6$, 25° C.) δ(ppm): 157.95, 157.31, 148.07, 90.03.

The wavelength of the infrared absorption spectrum of the compound of formula III (i.e., the compound shown in FIG. 7) prepared in Examples 1A-1D is: IR(KBr, γ/cm$^{-1}$): 3414 (m), 3231 (m), 2154 (s), 1600 (s), 1543 (s), 1403 (s), 1384 (s), 1313 (m), 1209 (m), 1131 (m).

The powder analysis results of the compound of formula III (i.e., the compound shown in FIG. 7) prepared in Examples 1A-1D is: DSC(160° C., 50° C.-250° C., 5° C.·min$^{-1}$).

The elemental analysis structure (measured value (calculated value) of the compound of formula III (i.e., the compound shown in FIG. 7) (molecular formula C$_4$HN$_9$O$_3$) prepared in Examples 1A-1D is: C, 21.62%; (21.53%), H, 0.47%; (0.45%), N, 56.61%; (56.50%), O, 21.22%; (21.51%).

Example 2

Figure 12:
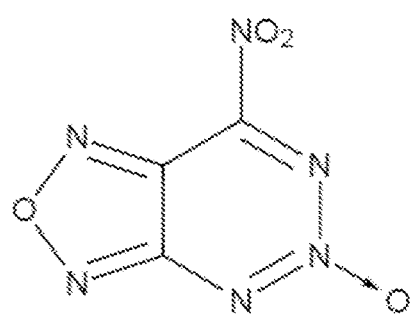
FIGS. 12, 14, 16, 18, 20, 22, 24, 26 are chemical structural diagrams of various embodiments of a compound of the present invention.
Figure 13:
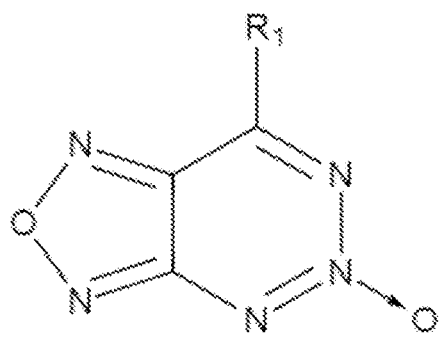
FIGS. 13, 15, 17, 19, 21, 23, 25, 27 are chemical structural diagrams showing partial structures of various embodiments of a compound of the present invention.

FIG. 12 is a chemical structural diagram of one embodiment of a compound of the present invention, and the specific name is: 7-nitro[1,2,5]oxadiazole[3,4-d][1,2,3]triazine 5-oxide, having a structure as shown in FIG. 1, specifically having a structure as shown in FIG. 3, and more specifically having a structure as shown in FIG. 13.

[Synthetic Method]

The specific synthesis method of the compound of Example 2 is described in detail below:

The first step reaction: synthesis of the precursor (1) Malononitrile and nitrite were dispersed in a solvent.

(2) A hydroxylamine compound was added to the reaction solution.

(3) After the addition of the hydroxylamine compound, the alkalis and ester compounds were added to continue the reaction.

(4) An acid and lead dioxide was added to the obtained compound, and the mixture was heated to reflux.

(5) Filtration was performed and the mother liquid was spin-dried to obtain the precursor of Example 2.

In the steps (1) to (3), the reaction temperature may be −20° C. to 130° C., for example, −20° C. to 40° C., for example, −20° C., −10° C., or 40° C. However, the present invention is not limited thereto, and it should be considered that any reaction temperature suitable for the reaction can be employed in the present invention.

In the step (1), the nitrite may be a compound of the formula MNO$_2$, wherein M is selected from one of NH$_4$, Li, Na, K, Rb and Cs, or a mixture of two or more thereof. For example, it may be sodium nitrite.

In the step (1), the solvent may be any one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, and the like, or a mixture of two or more thereof. However, the present invention is not limited thereto, and it should be considered that any solvent suitable for the reaction can be employed in the present invention.

In the step (1), the ratio of the volume of solvent to the mass of reactant may be, for example, the solvent volume: malononitrile=2 mL/g-2 mL/mg; for example, may be 10 mL/g, 15 mL/g, 35 mL/g, 75 mL/g or 400 mL/g. However, the present invention is not limited thereto, and it should be considered that any solvent ratio suitable for the reaction can be employed in the present invention.

In the step (2), the hydroxylamine compound may be hydroxylamine salts. For example, the hydroxylamine salts can be a compound of the formula $(NH_3OH)_aX_b$, wherein X is selected from one of F, Cl, Br, I, $NO_3$, $SO_4$, $HSO_4$, $CO_3$, $HCO_3$, HCOO, $CH_3COO$, $CF_3COO$, $(COO)_2$ and $CH_2(COO)_2$, or a mixture of two or more thereof. For example, the hydroxylamine compound may be hydroxylamine halide salts; for example, the hydroxylamine compound may be hydroxylamine hydrochloride.

In the steps (2) and (3), the reaction time may be from 2 hours to 24 hours, and may be, for example, 2 hours, 3 hours, 4 hours, 5 hours, 10 hours, or 24 hours. However, the present invention is not limited thereto, and it should be considered that any reaction time suitable for the reaction can be employed in the present invention.

In the step (3), the esters compound may be a compound of the formula $R^1COOR^2$, wherein $R^1$ and $R^2$ are selected from one of methyl, ethyl, propyl, isopropyl, butyl, sec-butyl, tert-butyl and various pentyl groups and hexyl groups, or a mixture of two or more thereof. However, the present invention is not limited thereto, and it should be considered that any suitable esters can be employed in the present invention.

In the step (3), the alkali may be a compound of the formula $M_a(OH)_b$, wherein M is selected from one of $NH_4$, Li, Na, K, Rb, Cs, Ca, Sr, and Ba, or two or more thereof. However, the present invention is not limited thereto, and it should be considered that any suitable alkalis can be employed in the present invention.

In the step (4), the type of the acid to be added may be nitric acid, sulfuric acid, hydrochloric acid, hydrobromic acid, hydrofluoric acid, hydroiodic acid, formic acid, acetic acid, acetic anhydride, oxalic acid, malonic acid, or trifluoroacetic acid or the like; it is possible to use a single acid as described above or a mixture of two or more acids. For example, it may be hydrochloric acid, formic acid, acetic anhydride, or trifluoroacetic acid; however, the present invention is not limited thereto, and it should be considered that any acid suitable for the reaction can be employed in the present invention.

In the step (4), the reaction temperature may be −20° C. to 130° C., for example, 40° C., 70° C., 100° C. (heated to reflux), 110° C., or 120° C. However, the present invention is not limited thereto, and it should be considered that any reaction temperature suitable for the reaction can be employed in the present invention.

The second step reaction: synthesis of the first intermediate (6) The precursor of Example 2 was dispersed in a solvent.

(7) A certain amount of salts and azides were added, and the mixture was reacted for a certain time at a certain reaction temperature.

(8) An acid was added, and the mixture was purified to obtain the first intermediate of Example 2.

In this part, the solvent used in the step (6), the salts and azides added and the reaction temperature and reaction time in the step (7), and the acid added in the step (8) can be referred to the reaction conditions described in the step 2 of the general synthesis method.

The third step reaction: synthesis of the second intermediate (9) The first intermediate of Example 2 was slowly added to a nitration system, and after the addition, the temperature of the reaction system was controlled to maintain the nitration reaction.

(10) The reaction was terminated and filtration was performed.

(11) Purification and drying were performed to give the second intermediate of Example 2.

In this part, the nitration system added and the reaction temperature in the step (9), and the manner of terminating the reaction in the step (10) can be referred to the reaction conditions described in the step 3 of the general synthesis method.

The fourth step reaction: synthesis of the product

(12) The second intermediate of Example 2 was dispersed in a solvent.

(13) A certain amount of strong ammonia solution was added, the reaction was carried out under reflux for a period of time, followed by cooling and filtration to obtain a solid.

(14) The solid was put into an oxidizing solution and the mixture was reacted for a period of time.

(15) The reaction was terminated, followed by filtration and purification to give the product of Example 2, i.e., the compound shown in FIG. 12.

In this part, the solvent used in the step (12), the concentration and proportion of the strong ammonia solution used and the reaction time in the step (13), and the selection of the oxidizing solution and the reaction time in the step (14) can be referred to the reaction conditions described in the step 4 C of the general synthesis method For a specific example of the above reaction, please refer to the following Example 2A.

Example 2A 6.66 g of malononitrile and 20.7 g of sodium nitrite were dispersed in 100 mL of water, the mixture was cooled in an ice water bath, then a 200 mL of aqueous solution containing 27.8 g of hydroxylamine hydrochloride was added dropwise thereto (completed in half an hour); the mixture was stood at −10° C. after the addition, then added with a 100 mL aqueous solution of sodium hydroxide (10.1 g) and 100 mL of ethyl acetate, and the mixture was reacted under stirring for 10 hours followed by filtration; the obtained solid was dissolved in 200 mL of diethyl ether, then 20 mL of acetic acid and 17.2 g of lead dioxide were added thereto, and the mixture was heated to reflux, followed by filtration, and the mother liquid was spin-dried.

The obtained solid was dispersed in 10 mL of water together with 3.6 g of ammonium fluoride and 12 g of sodium azide, the mixture was reacted at 75° C. for 7 hours, then cooled to room temperature, and hydrochloric acid was added dropwise thereto until the pH of the solution was 3.1, followed by filtration and washing with 5 mL of ice water, the obtained solid was dried to obtain 12.2 g of orange powder.

Then, 0.4 g of the obtained orange powder was added to a 6 mL mixed solution of 100% nitric acid/trifluoroacetic anhydride in a volume ratio of 1:1, the mixture was reacted at room temperature for 1 hour, and the reaction liquid was poured into 50 g of ice water, followed by stirring 0.5 hour, filtration, washing with 10 mL of ice water, and drying to obtain 0.51 g of a yellow powdery solid.

Then, the obtained solid was dissolved in 5 mL of methanol, and 4 mL of concentrated aqueous ammonia was added thereto, and the mixture was subjected to reflux reaction for 2 hours, cooled and filtered to give a pale yellow powdery product; the product was poured into 5 mL of a solvent mixture of concentrated sulfuric acid and 30% hydrogen peroxide in a volume ratio of 1:1, the mixture was reacted under stirring for 1 hour, followed by pouring into 20 g of ice, and filtering to obtain 0.44 g of an orange solid with a yield of 69%.

[Measurement Results]

Elemental analysis EA: measured value (theoretical value) C, 19.59%; (19.58%); N, 45.67%; (45.66%); O, 34.74%; (34.77%).

Infrared spectroscopy (IR spectroscopy) (KBr, $\gamma/cm^{-1}$): 3019 (m), 2790 (s), 1598 (s), 1535 (s), 1371 (s), 1341 (m), 1209 (m), 871 (m), 827 (m), 740 (s), 688 (m), 540 (w)

Example 3

Figure 14:
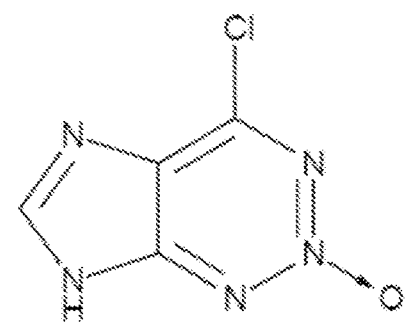
Figure 15:
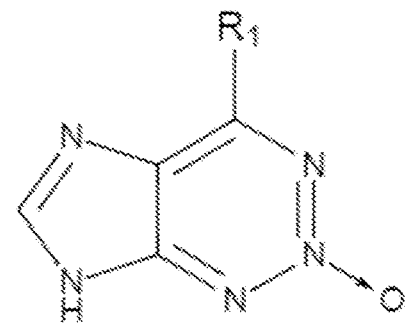

FIG. 14 is a chemical structural diagram of one embodiment of a compound of the present invention, and the specific name is: 4-chloro-7H-imidazole [4,5-d][1,2,3]triazine 2-oxide having a structure as shown in FIG. 1, specifically having a structure as shown in FIG. 3, and more specifically having a structure as shown in FIG. 15.

[Synthetic Method]

The specific synthesis method of the compound of Example 3 is specifically carried out by using 4-amino-5-cyanoimidazole as a precursor, and described in detail below:

The first step reaction: synthesis of the first intermediate (1) 4-amino-5-cyanoimidazole was dispersed in a solvent.

(2) A certain amount of salts and a certain amount of azides were added, and the mixture was reacted for a certain time at a certain reaction temperature.

(3) An acid was added, and the mixture was purified to obtain the first intermediate of Example 3.

In this part, the solvent used in the step (1), the salts and azides added and the reaction temperature and reaction time in the step (2), and the acid added in the step (3) can be referred to the reaction conditions described in the step 2 of the general synthesis method.

The second step reaction: synthesis of the second intermediate (4) The first intermediate of Example 3 was slowly added to a nitration system, the temperature of the reaction system was controlled after the addition, and the nitration reaction was maintained at a certain temperature for a certain period of time.

(5) The reaction was terminated, and the mixture was purified to obtain the second intermediate of Example 3.

In this part, the nitration system added and the reaction temperature in the step (4), and the manner of terminating the reaction in the step (5) can be referred to the reaction conditions described in the step 3 of the general synthesis method.

The third step reaction: synthesis of the product (6) The second intermediate of Example 3 was dispersed in a solvent.

(7) Chlorine gas flow was introduced and the mixture was reacted for a certain period of time at a certain temperature.

(8) Purification and drying were performed to give the product of Example 3, i.e., the compound shown in FIG. 14.

In this part, the solvent used in the step (6), the chlorine gas flow rate, the reaction temperature and the reaction time used in the step (7) can be referred to the reaction conditions described in the step 4 A of the general synthesis method.

For a specific example of the above reaction, please refer to the following Example 3A.

Example 3A 10.8 g of 4-amino-5-cyanoimidazole, 3.6 g of ammonium fluoride and 12 g of sodium azide were dispersed in 10 mL of water together, the mixture was reacted at 75° C. for 7 hours and then cooled to room temperature; hydrochloric acid was added dropwise thereto until the pH of the solution was 3.1, followed by filtering, washing with 5 mL of ice water, and drying the solid to give 11.3 g of brown powder.

Then 0.5 g of the obtained brown powder was added to a 20 mL mixed solution of 100% nitric acid/trifluoroacetic anhydride in a volume ratio of 1:1, the mixture was reacted at −10° C. for 4 hours, then the reaction liquid was poured into 50 g ice water, followed by stirring for 0.5 hour, filtering, washing with 20 mL of ice water, and drying to give 0.28 g of a yellow green powdery solid with a yield of 30%.

The obtained solid was dissolved in 8 mL of dichloromethane, then chlorine gas flow was introduced at a flow rate: 5 mL/min, the mixture was reacted at 70° C. for 1 hour, followed by filtration to obtain 0.17 g of a white powdery product with a yield of 30%.

[Measurement Results]

Elemental analysis EA: measured value (theoretical value) C, 27.79%; (28.01%); H, 1.12%; (1.18%); Cl, 20.61%; (20.67%); N, 40.77%; (40.83%); O, 9.29%; (9.33%).

Infrared spectroscopy (IR spectroscopy) (KBr, $\gamma/cm^{-1}$): 3321 (s), 3290 (m), 1577 (s), 1555 (s), 1366 (s), 1332 (m), 1220 (m), 996 (w), 871 (m), 827 (m), 765 (w), 621 (m).

Example 4

Figure 16:
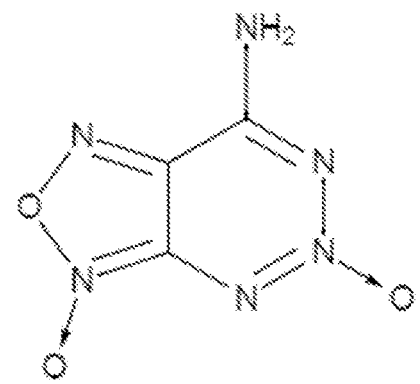
Figure 17:
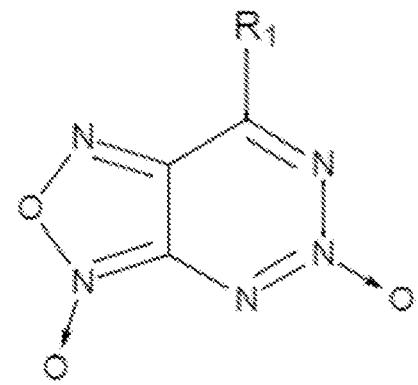

FIG. 16 is a chemical structural diagram of one embodiment of a compound of the present invention, and the specific name is: 7-amino-[1,2,5]oxadiazole [3,4-d][1,2,3] triazine 3,5-dioxide, having a structure as shown in FIG. 1, specifically having a structure as shown in FIG. 3, more specifically having a structure as shown in FIG. 17.

[Synthetic Method]

The specific synthesis method of the compound of Example 4 is described in detail below:

The first step reaction: synthesis of the precursor (1) Malononitrile and nitrite were dispersed in a solvent.

(2) An acid was added to the reaction solution, and the mixture was reacted, followed by purification to obtain the product.

(3) The obtained product was dispersed in the solvent.

(4) A hydroxylamine compound was added to the solvent, and the mixture was subjected to reflux reaction.

(5) Filtration was performed and the mother liquid was spin-dried to obtain the precursor of Example 4.

In the steps (1) to (4), the reaction temperature may be −20° C. to 130° C., for example, −20° C., −10° C., or 40° C. However, the present invention is not limited thereto, and it should be considered that any reaction temperature suitable for the reaction can be employed in the present invention.

In the step (1), the solvent may be any one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, and the like, or a mixture of two or more thereof. However, the present invention is not limited thereto, and it should be considered that any solvent suitable for the reaction can be employed in the present invention.

In the step (1), the ratio of the volume of solvent to the mass of reactant may be, for example, the solvent volume: malononitrile=2 mL/g-2 mL/mg; for example, may be 10 mL/g, 15 mL/g, 35 mL/g, 75 mL/g or 400 mL/g. However, the present invention is not limited thereto, and it should be considered that any solvent ratio suitable for the reaction can be employed in the present invention.

In the step (1), the nitrite may be a compound of the formula $MNO_2$, wherein M is selected from one of $NH_4$, Li, Na, K, Rb and Cs, or a mixture of two or more thereof. For example, it may be sodium nitrite.

In the step (2), the types of the acid to be added may be nitric acid, sulfuric acid, hydrochloric acid, hydrobromic acid, hydrofluoric acid, hydroiodic acid, formic acid, acetic acid, acetic anhydride, oxalic acid, malonic acid, or trifluoroacetic acid or the like; it is possible to use a single acid as described above or a mixture of two or more acids. For example, it may be hydrochloric acid, formic acid, acetic anhydride, or trifluoroacetic acid; however, the present invention is not limited thereto, and it should be considered that any acid suitable for the reaction can be employed in the present invention.

In the step (4), the hydroxylamine compound may be hydroxylamine salts. For example, the hydroxylamine salts can be a compound of the formula $(NH_3OH)_aX_b$, wherein X is selected from one of F, Cl, Br, I, $NO_3$, $SO_4$, $HSO_4$, $CO_3$, $HCO_3$, HCOO, $CH_3COO$, $CF_3COO$, $(COO)_2$ and $CH_2(COO)_2$, or a mixture of two or more thereof. For example, the hydroxylamine compound may be hydroxylamine halide salts; for example, the hydroxylamine compound may be hydroxylamine hydrochloride.

In the steps (2) and (4), the reaction time may be from 2 hours to 24 hours, and may be, for example, 2 hours, 3 hours, 4 hours, 5 hours, 10 hours, or 24 hours. However, the present invention is not limited thereto, and it should be considered that any reaction time suitable for the reaction can be employed in the present invention.

The second step reaction: synthesis of the first intermediate (6) The precursor of Example 4 was dispersed in a solvent.

(7) A certain amount of salts and azides were added, and the mixture was reacted for a certain time at a certain reaction temperature.

(8) An acid was added, and the mixture was purified to obtain the first intermediate of Example 4.

In this part, the solvent used in the step (6), the salts and azides added and the reaction temperature and the reaction time in the step (7), and the acid added in the step (8) can be referred to the reaction conditions described in the step 2 of the general synthesis method.

The third step reaction: synthesis of the second intermediate (9) The first intermediate of Example 4 was slowly added to a nitration system, and after the addition, the temperature of the reaction system was controlled to maintain the nitration reaction.

(10) The reaction was terminated, followed by filtration and purification to give the second intermediate of Example 4.

In this part, the nitration system added and the reaction temperature in the step (9), and the manner of terminating the reaction in the step (10) can be referred to the reaction conditions described in the step 3 of the general synthesis method.

The fourth step reaction: synthesis of the product

(11) The second intermediate of Example 4 was dispersed in a solvent.

(12) A certain amount of strong ammonia solution was added, the reaction was carried out under reflux for a period of time, followed by cooling.

(13) Filtration and purification were performed to give the product of Example 4, i.e., the compound shown in FIG. 16.

In this part, the solvent used in the step (11), the concentration and proportion of the strong ammonia solution used and the reaction time in the step (12), and the selection of the oxidizing solution and the reaction time in the step (14) can be referred to the reaction conditions described in the step 4B of the general synthesis method For a specific example of the above reaction, please refer to the following Example 4A.

Example 4A 6.66 g of malononitrile and 20.7 g of sodium nitrite were dispersed in 100 mL of water, 5 mL of acetic acid was added dropwise thereto, and the mixture was reacted at room temperature for 3 hours, and then extracted with 200 mL of ethyl acetate, followed by spin-drying the ethyl acetate layer; the obtained material was dispersed in 200 mL of ethanol, 27.8 g of hydroxylamine hydrochloride was added thereto, and the mixture was refluxed for 4 hours, followed by filtering, and spin-drying the mother liquid.

The solid obtained was dispersed in 300 mL of a mixed solvent of acetone and methanol in a volume ratio of 4:1 at room temperature, followed by adding 13 g of cobaltous chloride and 15.2 g of sodium azide in batches, then the mixture was reacted for 10 hours under reflux, and trifluoroacetic acid was added dropwise thereto until the pH of the solution was 2.4, followed by filtering, washing with 30 mL of ice water, then washing with 30 mL of diethyl ether, and drying the solid to give white powder.

Then, the obtained white powder was added to 200 mL of acetonitrile added with 11.1 g of nitronium tetrafluoroborate, then the mixture was reacted for 4 hours at 4° C., the reaction liquid was poured into 50 g of ice water, followed by stirring for 0.5 hour, filtering, washing with 20 mL of ice water, then washing with 10 mL of petroleum ether and drying to give 12.1 g of a white powdery solid with a yield of 75%.

Then, the obtained solid was dissolved in 150 mL of methanol, and 140 mL of concentrated aqueous ammonia was added thereto, and the mixture was subjected to reflux reaction for 2 hours, followed by cooling, and filtering to give 6.97 g of a final pale yellow powdery product with a yield of 40%.

[Measurement Results]

Elemental analysis EA: measured value (theoretical value) C, 21.19%; (21.18%); H, 1.16%; (1.19%); N, 49.33%; (49.41%); O, 28.19%; (28.22%).

Infrared spectroscopy (IR spectroscopy) (KBr, $\gamma/cm^{-1}$): 3434 (s), 3134 (m), 3019 (m), 2790 (s), 2321 (m), 1571 (s), 1512 (s), 1380 (s), 1321 (m), 836 (m), 721 (s), 644 (m).

Example 5

Figure 18:
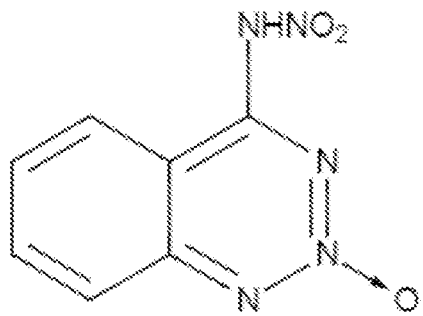
Figure 19:
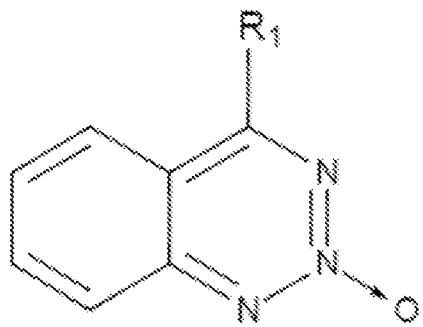

FIG. 18 is a chemical structural diagram of one embodiment of a compound of the present invention, and the specific name is: 4-nitroaminobenzo[d][1,2,3]triazine 2-oxide, having the structure shown in FIG. 1, specifically having the structure shown in FIG. 4, and more specifically having the structure shown in FIG. 19.

[Synthetic Method]

The specific synthesis method of the compound of Example 5 is specifically carried out by using 1-amino-2-cyano-benzene as a precursor, and is described in detail below:

The first step reaction: synthesis of the first intermediate (1) 1-amino-2-cyano-benzene was dispersed in a solvent.

(2) A certain amount of salts and a certain amount of azides were added thereto, and the mixture was reacted for a certain time at a certain reaction temperature.

(3) An acid was added, followed by purification to obtain the first intermediate of Example 5.

In this part, the solvent used in the step (1), the salts and azides added and the reaction temperature and the reaction time in the step (2), and the acid added in the step (3) can be referred to the reaction conditions described in the step 2 of the general synthesis method.

The second step reaction: synthesis of the second intermediate (4) The first intermediate of Example 5 was slowly added to a nitration system, and after the addition, the temperature of the reaction system was controlled, and the nitration reaction was maintained at a certain temperature for a certain period of time.

(5) The reaction was terminated, followed by filtration and purification to give the second intermediate of Example 5.

In this part, the nitration system added and the reaction temperature in the step (4), and the manner of terminating the reaction in the step (5) can be referred to the reaction conditions described in the step 3 of the general synthesis method.

The third step reaction: synthesis of the product (6) The second intermediate was dispersed in a solvent.

(7) A certain amount of strong ammonia solution was added, and the reaction was carried out under reflux for a period of time.

(8) Cooling and filtering were performed to give a solid.

(9) The solid was put into the nitration system and the mixture was stirred for a period of time.

(10) The reaction was terminated, followed by filtration and purification to give the product of Example 5, i.e., the compound shown in FIG. 18.

In this part, the solvent used in the step (6), the concentration and proportion of the strong ammonia solution used and the reaction time in the step (7), the nitration system added and the reaction temperature in the step (9), and the manner of terminating the reaction in the step (10) can be referred to the reaction conditions described in the step 4 D of the general synthesis method For a specific example of the above reaction, please refer to the following Example 5A.

Example 5A 11.8 g of 1-amino-2-cyanobenzene was dispersed in 300 mL of a solvent obtained by mixing acetone and methanol in a volume ratio of 4:1, followed by adding 13 g of cobaltous chloride and 15.2 g of sodium azide in batches, then, the mixture was subjected to reflux reaction for 10 hours, and trifluoroacetic acid was added dropwise thereto until the pH of the solution was 3, followed by filtering, washing with 30 mL of ice water, then washing with 30 mL of diethyl ether, and drying the solid to give gray powder.

Then, the obtained gray powder was added to 180 mL of acetonitrile added with 13.3 g of nitronium tetrafluoroborate, and then the mixture was reacted at −5° C. for 7 hours; the reaction liquid was poured into 50 g of ice water, stirred for 0.5 hour, followed by filtering, washing with 20 mL ice water, then washing with 10 mL of petroleum ether, and drying to give a beige powdery solid.

Then, the obtained solid was dissolved in 150 mL of methanol, 140 mL of concentrated aqueous ammonia was added thereto, and the mixture was subjected to reflux reaction for 2 hours, followed by cooling and filtering to give a pale yellow powdery solid; the obtained solid was added to 100 mL of fuming nitric acid, the mixture was stirred for 2 hours, then poured into 300 g of ice, followed by filtering, and washing with water to give 11.5 g of a yellow solid.

[Measurement Results]

Elemental analysis EA: measured value (theoretical value) C, 40.51%; (40.59%); H, 2.39 (2.43); N, 33.86%; (33.81%); O, 23.27%; (23.17%)

Infrared spectroscopy (IR spectroscopy) (KBr, $\gamma/cm^{-1}$): 3435 (m), 3021 (w), 2824 (s), 2708 (s), 1602 (s), 1581 (s), 1535 (s), 1500 (s), 1453 (m), 1369 (s), 1323 (m), 908 (w), 701 (m), 634 (m).

Example 6

Figure 20:
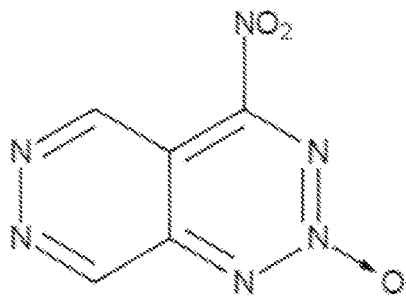
Figure 21:
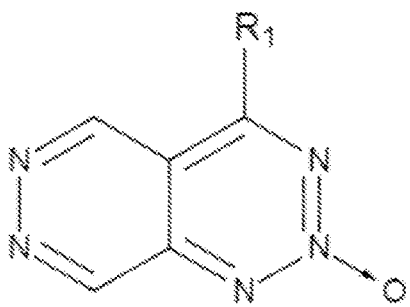

FIG. 20 is a chemical structural diagram of one embodiment of a compound of the present invention, and the specific name is: 4-nitropyridazine[4,5-d][1,2,3]triazine 2-oxide, having a structure as shown in FIG. 1, specifically having a structure as shown in FIG. 4, and more specifically having a structure as shown in FIG. 21.

[Synthetic Method]

The specific synthesis method of the compound of Example 6 is specifically carried out by using 4-amino-5-cyanopyridazine as a precursor, and is described in detail below:

The first step reaction: synthesis of the first intermediate (1) 4-amino-5-cyanopyridazine was dispersed in a solvent.

(2) A certain amount of salts and azides were added, and the mixture was reacted for a certain time at a certain reaction temperature.

(3) An acid was added, and the mixture was purified to obtain the first intermediate of Example 6.

In this part, the solvent used in the step (1), the salts and azides added and the reaction temperature and the reaction time in the step (2), and the acid added in the step (3) can be referred to the reaction conditions described in the step 2 of the general synthesis method.

The second step reaction: synthesis of the second intermediate (4) The first intermediate of Example 6 was slowly added to a nitration system, and after the addition, the temperature of the reaction system was controlled to maintain the nitration reaction.

(5) The reaction was terminated, followed by filtration and purification to give the second intermediate of Example 6.

In this part, the nitration system added and the reaction temperature in the step (4), and the manner of terminating the reaction in the step (5) can be referred to the reaction conditions described in the step 3 of the general synthesis method.

The third step reaction: synthesis of the product (6) The second intermediate of Example 6 was dispersed in a solvent.

(7) A certain amount of strong ammonia solution was added, the reaction was carried out under reflux for a period of time, followed by cooling and filtration to obtain a solid.

(8) The solid was put into an oxidizing solution and the mixture was reacted for a period of time.

(9) The reaction was terminated, followed by filtration and purification to give the product of Example 6, i.e., the compound shown in FIG. 20.

In this part, the solvent used in the step (6), the concentration and proportion of the strong ammonia solution used and the reaction time in the step (7), and the selection of the oxidizing solution and the reaction time in the step (8) can be referred to the reaction conditions described in the step 4 C of the general synthesis method For a specific example of the above reaction, please refer to the following Example 6A.

Example 6A 11.1 g of 4-amino-5-cyano-pyridazine was dispersed in 50 mL of water together with 5.1 g of ammonium chloride and 11 g of ammonium azide, the mixture was reacted at 85° C. for 7 hours, and then cooled to room temperature; hydrochloric acid was added dropwise into the mixture until the pH of the solution was 1, followed by filtration, washing with 15 mL of ice water, and drying the solid to give 12.8 g of brown powder.

Then, 0.4 g of the obtained brown powder was added to a 6 mL mixed solution of 100% nitric acid/trifluoroacetic anhydride in a volume ratio of 1:1, the mixture was reacted at room temperature for 1 hour, then the reaction liquid was poured into 50 g ice water, followed by stirring for 0.5 hour, filtering, washing with 10 mL of ice water, and drying to give 0.55 g of a yellow green powdery solid.

Then, the obtained solid was dissolved in 5 mL of methanol, 4 mL of concentrated aqueous ammonia was added thereto, and the mixture was refluxed for 2 hours, followed by cooling and filtering to give a pale yellow powdery product; the obtained product was poured into 5 mL of a mixed solvent of concentrated sulfuric acid and 30% hydrogen peroxide in a volume ratio of 1:1, and the mixture was stirred for 1 hour, followed by pouring into 20 g of ice, and filtering to obtain a yellow solid.

[Measurement Results]

Elemental analysis EA: measured value (theoretical value) C, 30.91%; (30.94%); H, 1.01%; (1.04%); N, 43.12%; (43.30%); O, 24.63% (24.73%).

Infrared spectroscopy (IR spectroscopy) (KBr, $\gamma/cm^{-1}$): 3091 (s), 1592 (s), 1541 (s), 1366 (s), 1339 (m), 881 (m), 831 (m), 712 (s).

Example 7

Figure 22:
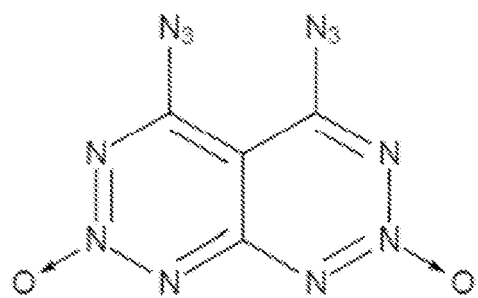
Figure 23:
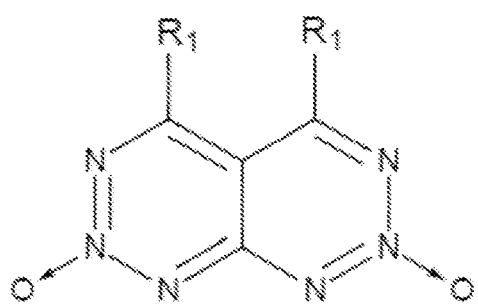

FIG. 22 is a chemical structural diagram of one embodiment of a compound of the present invention, and the specific name is: 4,5-diazide-[1,2,3]triazine[4,5-d][1,2,3]triazine 2,7-oxide, having a structure as shown in FIG. 1, specifically having a structure as shown in FIG. 4, more specifically having a structure as shown in FIG. 23.

[Synthetic Method]

The specific synthesis method of the compound of Example 7 is specifically carried out by using 3,3-diamino-2-(1H-tetrazol-5-yl)propanenitrile as a precursor, and is described in detail below:

The first step reaction: synthesis of the first intermediate (1) 3,3-diamino-2-(1H-tetrazol-5-yl)propanenitrile was dispersed in a solvent.

(2) A certain amount of salts and azides were added, and the mixture was reacted for a certain time at a certain reaction temperature.

(3) An acid was added, and the mixture was purified to obtain the first intermediate of Example 7.

In this part, the solvent used in the step (1), the salts and azides added and the reaction temperature and the reaction time in the step (2), and the acid added in the step (3) can be referred to the reaction conditions described in the step 2 of the general synthesis method.

The second step reaction: synthesis of the product (4) The first intermediate of Example 7 was slowly added to a nitration system, and after the addition, the temperature of the reaction system was controlled to maintain the nitration reaction.

(5) The reaction was terminated, followed by filtration and purification to give the second intermediate of Example 7, which is the compound shown in FIG. 22.

In this part, the nitration system added and the reaction temperature in the step (4), and the manner of terminating the reaction in the step (5) can be referred to the reaction conditions described in the step 3 of the general synthesis method.

For a specific example of the above reaction, please refer to the following Example 7A.

Example 7A 15.3 g of 3,3-diamino-2-(1H-tetrazol-5-yl)propanenitrile, 5.1 g of dimethylamine hydrochloride and 11 g of ammonium azide were dispersed in 50 mL of DMF together, the mixture was reacted for 3 hours at 85° C., followed by filtration; the mother liquid was concentrated to 10 mL, and then 50 mL of water was added thereto, followed by dropwise addition of hydrochloric acid until the pH of the solution was 2, followed by filtration, washing with 15 mL of ice water, and drying the solid to give 14.1 g of gray powder.

Then, 0.4 g of the obtained gray powder was added into a mixed solution of 3 mL of 100% nitric acid and 3 mL of concentrated sulfuric acid, the mixture reacted for 4 hours at 60° C., the reaction liquid was poured into 20 g of ice water, followed by stirring for 0.5 hour, and extracting with 100 mL of ethyl acetate, the organic layer was spin-dried and dried to give 0.50 g of a brown solid.

[Measurement Results]

Elemental analysis EA: measured value (theoretical value) C, 19.38%; (19.38%); H, 0.01%; (0.00%); N, 67.77%; (67.74%); O, 12.93% (12.90%).

Infrared spectroscopy (IR spectroscopy) (KBr, $\gamma/cm^{-1}$): 3110 (s), 2163 (s), 1855 (m), 1313 (s), 899 (m), 842 (m), 659 (s).

Example 8

Figure 24:
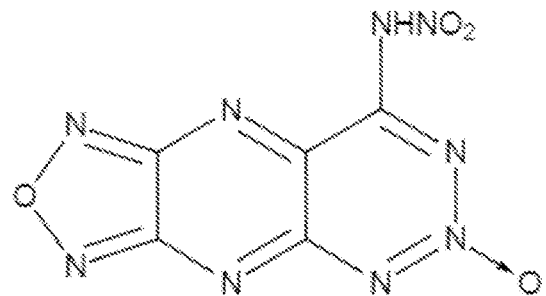
Figure 25:
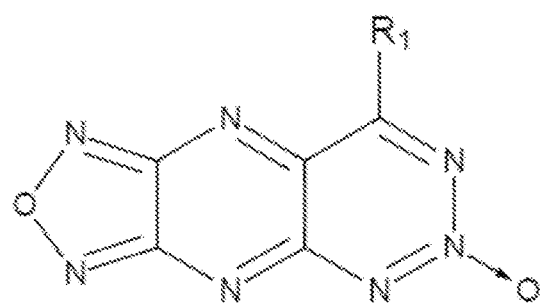

FIG. 24 is a chemical structural diagram of one embodiment of a compound of the present invention, and the specific name is: 8-nitroamino [1,2,5]oxadiazole [3',4':5,6] pyrazine [2,3-d][1,2,3]triazine 6-oxide, having a structure as shown in FIG. 1, specifically having a structure as shown in FIG. 5, more specifically having the structure shown in FIG. 25.

[Synthetic Method]

The specific synthesis method of the compound of Example 8 is described in detail below:

The first step reaction: synthesis of precursors (1) 3,4-diaminofurazan and oxalic acid were dispersed in a solvent.

(2) An acid was added and the mixture was reacted.

(3) The obtained product was dissolved in thionyl chloride, then N,N-dimethylformamide was added dropwise thereto, and the mixture was refluxed.

(4) The reaction was terminated, followed by filtration to give a solid.

(5) The obtained solid was dispersed in a solvent, a nitride was added, and the reaction was carried out under reflux.

(6) Cooling and filtering were performed, followed by spin-drying the mother liquor.

(7) The obtained solid was dispersed in a solvent, strong ammonia solution was added or ammonia gas flow was introduced, and the reaction was carried out under reflux.

(8) Cooling and filtering were performed, followed by spin-drying the mother liquor to obtain the precursor material of Example 8.

In the steps (1) to (3), the reaction temperature may be −20° C. to 130° C., for example, −40° C., −70° C., 100° C. (heated to reflux), 110° C., or 120° C. However, the present invention is not limited thereto, and it should be considered that any reaction temperature suitable for the reaction can be employed in the present invention.

In the step (1) or (5), the solvent may be any one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, and the like, or a mixture of two or more thereof. However, the present invention is not limited thereto, and it should be considered that any solvent suitable for the reaction can be employed in the present invention.

In the step (1), the ratio of the volume of solvent to the mass of reactant may be, for example, the solvent volume: 3,4-diaminofurazan=2 mL/g-2 mL/mg; for example, may be 9.9 mL/g, 10 mL/g, 15 mL/g, 35 mL/g, 75 mL/g or 400 mL/g. However, the present invention is not limited thereto, and it should be considered that any solvent ratio suitable for the reaction can be employed in the present invention.

In the step (2), the types of the acid to be added may be concentrated hydrochloric acid, concentrated hydrobromic acid, concentrated hydrofluoric acid, concentrated hydroiodic acid or the like; it is possible to use a single acid as described above or a mixture of two or more acids. However, the present invention is not limited thereto, and it should be considered that any acid suitable for the reaction can be employed in the present invention.

In the step (3), the reaction time may be from 0.5 hour to 12 hours, and may be, for example, from 0.5 hour to 4 hours, and may be, for example, from 1 hour to 4 hours, and may be, for example, 0.5 hour, 1 hour, 2 hours, and 4 hours. However, the present invention is not limited thereto, and it should be considered that any reaction time suitable for the reaction can be employed in the present invention.

In the step (5), the nitride may be a compound of the general formula $R_a(N)_b$, wherein R is selected from one of Li, Na, K, Rb, Cu, Fe, Ag, Au, Pb, Cd, Ni and H, or a mixture of two or more thereof, and the corresponding a and b are selected.

In the step (5), the reaction time may be from 0.5 hour to 12 hours, and may be, for example, from 0.5 hour to 4 hours, and may be, for example, from 1 hour to 4 hours, and may be, for example, 0.5 hour, 1 hour, 2 hours, and 4 hours. However, the present invention is not limited thereto, and it should be considered that any reaction time suitable for the reaction can be employed in the present invention.

In the step (7), the solvent may be an ammonia gas flow-insoluble or ammonia gas flow-indissolvable solvent, or a strong ammonia solution-soluble solvent. For example, when the ammonia gas flow was used in the step (7), the solvent may be any one of dichloromethane, chloroform, acetone, benzene, toluene, xylene, or the like, or a mixture of two or more thereof; When strong ammonia solution was used in the step (7), the solvent may be any one of methanol, ethanol, water, isopropyl alcohol, ethylene glycol, glycerin, acetone, or the like, or a mixture of two or more thereof. For example, the step (7) may employ an ammonia gas flow, and the solvent may be dichloromethane.

the reaction time may be from 0.5 hour to 12 hours, and may be, for example, from 0.5 hour to 4 hours, and may be, for example, from 1 hour to 4 hours, and may be, for example, 0.5 hour, 1 hour, 2 hours, and 4 hours. However, the present invention is not limited thereto, and it should be considered that any reaction time suitable for the reaction can be employed in the present invention.

The second step reaction: synthesis of the first intermediate (9) The precursor of Example 8 was dispersed in a solvent.

(10) A certain amount of salts and azides were added, and the mixture was reacted for a certain time at a certain reaction temperature.

(11) An acid was added, and the mixture was purified to obtain the first intermediate of Example 8.

In this part, the solvent used in the step (9), the salts and azides added and the reaction temperature and reaction time in the step (10), and the acid added in the step (11) can be referred to the reaction conditions described in the step 2 of the general synthesis method.

The third step reaction: synthesis of the second intermediate

(12) The first intermediate of Example 8 was slowly added to a nitration system, and after the addition, the temperature of the reaction system was controlled to maintain the nitration reaction.

(13) The reaction was terminated, followed by filtration and purification to give the second intermediate of Example 8.

In this part, the nitration system added and the reaction temperature in the step (12), and the manner of terminating the reaction in the step (13) can be referred to the reaction conditions described in the step 3 of the general synthesis method.

The fourth step reaction: synthesis of the product

(14) The second intermediate was dispersed in a solvent.

(15) A certain amount of strong ammonia solution was added, the reaction was carried out under reflux for a period of time.

(16) Cooling and filtration were performed to obtain a solid

(17) The obtained solid was put into the nitration system and the mixture was stirred for a period of time.

(18) The reaction was terminated, followed by filtration and purification to give the product of Example 8, i.e., the compound shown in FIG. 24.

In this part, the solvent used in the step (14), the concentration and proportion of the strong ammonia solution used and the reaction time in the step (15), and the selection of the nitration system and the reaction time in the step (18) can be referred to the reaction conditions described in the step 4 D of the general synthesis method For a specific example of the above reaction, please refer to the following Example 8A.

Example 8A 10.1 g of 3,4-diaminofurazan and 15.1 g of oxalic acid were dispersed in 100 mL of water, and then 20 mL of concentrated hydrochloric acid was added thereto under an ice water bath, and the mixture was heated to reflux for 4 hours, followed by cooling and filtering to give a solid product.

The solid was dissolved in 70 mL of thionyl chloride, then 5 mL of N,N-dimethylformamide was added dropwise thereto, and the mixture was heated to reflux for 4 hours, followed by pouring into 200 g of ice water, and filtering to give a solid; then, the solid was dissolved in 50 mL of acetone, 3.9 g of sodium nitride was added thereto, and the mixture was heated to reflux for 1 hour, followed by cooling, filtering, and spin-drying the mother liquid; the obtained solid was dissolved in 60 mL of dichloromethane, ammonia gas flow was introduced at a flow rate 5 mL/min, the mixture was subjected to reflux reaction for 4 hours, followed by cooling, filtering, and spin-drying the mother liquid.

The obtained solid was dispersed in 300 mL of a mixed solvent of acetone and methanol in a volume ratio of 4:1, then 13 g of cobaltous chloride and 15.2 g of sodium azide were added in batches, then the mixture was subjected to reflux reaction for 10 hours, and dilute sulfuric acid was added dropwise thereto until the pH of the solution was 3.3, followed by filtering, washing with 30 mL of ice water, then washing with 30 mL of diethyl ether, and drying the solid to give pink powder.

Then, the obtained pink powder was added into 180 mL of acetonitrile added with 13.3 g of nitronium tetrafluoroborate, and the mixture was reacted for 3 hours at 0° C.; the reaction liquid was poured into 50 g of ice water, followed by stirring for 0.5 hour, filtering, washing with 20 mL of ice water, then washing with 10 mL of petroleum ether, and drying to give a pale yellow powdery solid.

Then, the obtained solid was dissolved in 90 mL of methanol, 900 mL of concentrated aqueous ammonia was added thereto, and the mixture was refluxed for 2 hours, followed by cooling and filtering to give an orange powdery solid; the obtained solid was added to 60 mL of fuming nitric acid, followed by stirring for 2 hours, pouring into 200 g of ice, filtering, and washing with water to give 7.7 g of a yellow solid.

[Measurement Results]

Elemental analysis EA: measured value (theoretical value) C, 23.89%; (23.91%); H, 0.35%; (0.40%); N, 50.23%; (50.20%); O, 25.44% (25.48%).

Infrared spectroscopy (IR spectroscopy) (KBr, $\gamma/cm^{-1}$): 3011 (s), 2182 (w), 2147 (m), 1591 (s), 1522 (s), 1331 (s), 1304 (m), 851 (m), 671 (s).

Example 9

Figure 26:
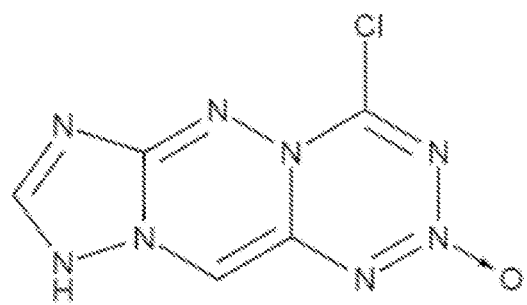
Figure 27:
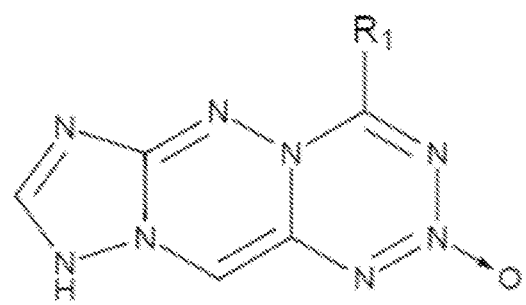

FIG. 26 is a chemical structural diagram of one embodiment of a compound of the present invention, and the specific name is: 2-oxo-4-chloro-9H-[1,2,4]triazole[5'-1':3,4][1,2,4]triazine[6,1-d][1,2,3,5]tetrazine, having the structure shown in FIG. 1, specifically having the structure shown in FIG. 5, more specifically, having the structure shown in FIG. 27.

[Synthetic Method]

The specific synthesis method of the compound of Example 9 is described in detail below:

The first step reaction: synthesis of the precursor (1) 3-amino-1,2,4-triazole was dispersed in a solvent.

(2) Sodium nitroacetonitrile salt was added and the mixture was subjected to reflux reaction.

(3) Cooling and filtering were performed, and the mother liquid was spin-dried to obtain the precursor of Example 9.

In the step (1), the solvent may be any one of N,N-dimethylformamide, dimethyl sulfoxide, tetrahydrofuran, acetonitrile, dichloromethane, chloroform, methanol, ethanol, water, isopropanol, ethylene glycol, ethylene glycol monomethyl ether, ethylene glycol monoethyl ether, ethylene glycol monobutyl ether, glycerin, acetone, triethanolamine, pyridine, benzene, toluene, xylene, and the like, or a mixture of two or more thereof. For example, it may be acetonitrile. However, the present invention is not limited thereto, and it should be considered that any solvent suitable for the reaction can be employed in the present invention.

In the step (1), the ratio of the volume of solvent to the mass of reactant may be, for example, the solvent volume: 3-amino-1,2,4-triazole=2 mL/g-2 mL/mg; for example, it may be 5.95 mL/g, 10 mL/g, 15 mL/g, 35 mL/g, 75 mL/g or 400 mL/g. However, the present invention is not limited thereto, and it should be considered that any solvent ratio suitable for the reaction can be employed in the present invention.

The nitroacetonitrile compound in the step (2) may be nitroacetonitrile salts. For example, the nitroacetonitrile compound may be a compound of the formula $M_a(CH(NO_2)CN)_b$, wherein M is selected from one of Li, Na, K, Rb, or Cs, or a mixture of two or more thereof. Specifically, the nitroacetonitrile compound may be a sodium nitroacetonitrile salt.

The second step reaction: synthesis of the first intermediate (4) The precursor of Example 9 was dispersed in a solvent.

(5) A certain amount of salts and azides were added, and the mixture was reacted for a certain time at a certain reaction temperature.

(6) An acid was added, and the mixture was purified to obtain the first intermediate of Example 9.

In this part, the solvent used in the step (4), the salts and azides added and the reaction temperature and reaction time in the step (5), and the acid added in the step (6) can be referred to the reaction conditions described in the step 2 of the general synthesis method.

The third step reaction: synthesis of the second intermediate (7) The first intermediate of Example 9 was slowly added to a nitration system, and after the addition, the temperature of the reaction system was controlled to maintain the nitration reaction.

(8) The reaction was terminated, followed by purification to give the second intermediate of Example 9.

In this part, the nitration system added and the reaction temperature in the step (7), and the manner of terminating the reaction in the step (8) can be referred to the reaction conditions described in the step 3 of the general synthesis method.

The fourth step reaction: synthesis of the product (9) The second intermediate of Example 9 was dispersed in a solvent.

(10) Chlorine gas flow was introduced and the mixture was reacted for a certain period of time at a certain temperature.

(11) Purification and drying were performed to give the product of Example 9, i.e., the compound shown in FIG. 26.

In this part, the solvent used in the step (9), the chlorine gas flow rate, the reaction temperature and the reaction time used in the step (10) can be referred to the reaction conditions described in the step 4 A of the general synthesis method.

For a specific example of the above reaction, please refer to the following Example 9A Example 9A 8.4 g of 3-amino-1,2,4-triazole was dispersed in 50 mL of acetonitrile, then 12.1 g of sodium nitroacetonitrile was added thereto, and the mixture was heated to reflux for 3 hours, followed by cooling, filtering, and spin-drying the mother liquid.

The obtained solid, 3.6 g of ammonium nitrate and 15.1 g of sodium azide were dispersed in 100 mL of water, then the mixture was reacted for 7 hours at 75° C., and cooled to room temperature; hydrochloric acid was added dropwise thereto until the pH of the solution was 3.1, followed by filtering, washing with 5 mL of ice water, and drying the solid to give 11.3 g of brown powder.

Then, 0.5 g of the obtained brown powder was added to a 20 mL mixed solution of 100% nitric acid/trifluoroacetic anhydride in a volume ratio of 1:1, and the mixture was reacted for 4 hours at −10° C.; the reaction liquid was poured into 50 g ice water, followed by stirring for 0.5 hour, filtering, washing with 20 mL of ice water, and drying to give 0.28 g of a yellow green powdery solid with a yield of 30%.

The obtained solid was dissolved in 20 mL of dichloromethane, then chlorine gas flow was introduced at a flow rate of 5 mL/min, and the mixture reacted for 1 hour at 60° C., followed by filtering to obtain 0.17 g of a white powdery product with a yield of 30%.

[Measurement Results]

Elemental analysis EA: measured value (theoretical value) C, 26.41%; (26.50%); H, 1.28%; (1.33%); Cl, 15.59%; (15.65%); N, 49.42%; (49.45%); O, 7.10%; (7.06%).

Infrared spectroscopy (IR spectroscopy) (KBr, $\gamma/cm^{-1}$): 3011 (s), 2280 (w), 2096 (m), 1571 (s), 1379 (s), 901 (m), 735 (s), 610 (w).

Determination of the Properties of the Compound as a Primer

[Determination of Minimum Initiating Charge I]

Performed in accordance with the standards set forth in Chinese National Military Standard GJB 5891.19-2006; specifically, followed these steps:

(1) The primer to be determined (for example, the one to be determined in the compounds of Examples 1-9), lead 2,4,6-trinitroresorcinate (in accordance with Chinese Industrial Standard WJ 617), and RDX (cyclotrimethylenetrinitramine) (in accordance with Chinese National Military Standard GJB 296A-1995) were put in a water bath or oil bath oven respectively, heated for 2 hours at 60° C.±2° C., then put in a dryer and cooled to room temperature for later use.

(2) 0.030 g of RDX treated by the step (1) was weighed to the nearest 0.0002 g using an analytical balance, put in a copper tube (5.1 mm in diameter, 8.2 mm in height), and pressed at a pressure of 117.6 MPa.

(3) 0.030 g of lead 2,4,6-trinitroresorcinate (that may not be used as a primer for the tested agents that can be directly ignited by the electric ignition head) treated in step (1), 0.020 g of RDX and the tested primer with the charge to be measured were weighed separately, to the nearest 0.0002 g, in turn placed in an aluminum reinforced cap (in the tight fit with the copper tube) with a silk pad (401 #plain silk according to Chinese Industrial Standard FZ 66201), and pressed at a pressure of 49.0 MPa and recorded.

(4) 0.020 g of RDX was weighed to the nearest 0.0002 g, the weighed RDX and the aluminum reinforced cap pressed in the step (3) were packed into the copper tube in the step (2); 10 samples were pressed at a pressure of 49.0 MPa and numbered, and the quality of the measured initiating charge for each number was recorded for later use.

Figure 28:
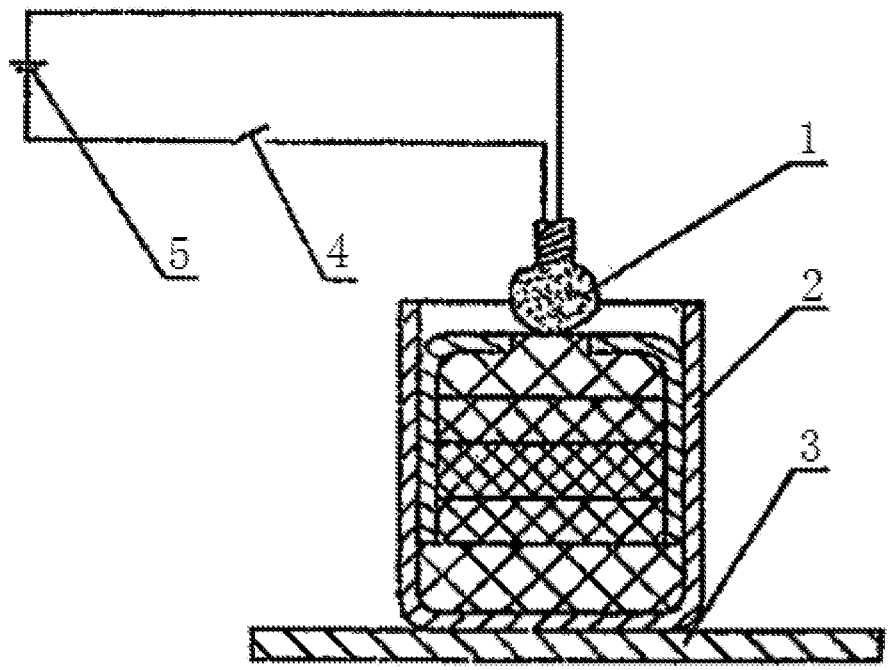
FIG. 28 is a diagram showing the apparatus for determining the minimum initiating charge of a compound of the present invention.

(5) As shown in FIG. 28, the packed sample 2 was placed on the lead plate 3 (35 mm in diameter, and 2 mm in thickness corresponding to Chinese Industrial Standard WJ 580), and on the other hand, the lead plate was connected to electric ignition head 1, then placed in a DC power supply circuit with power supply 4 and switch 5.

(6) The switch 5 was turned on to power on the power supply 4 and to detonate the sample. Whether the detonator was successfully detonated and the lead plate was broken down were checked.

(7) A blast hole on the lead plate was measured: the full explosion meant the diameter of the blast hole not less than the outer diameter of the sample; the half-explosion meant the diameter of the blast hole smaller than the outer diameter of the sample. If several test samples in the continuous test were fully exploded, the charge of the tested primer may be appropriately reduced and then tested; if the samples were half exploded, the charge of the test primer may be appropriately increased, until the minimum initiating charge of the tested primer for full explosion of several test samples in the continuous test had been found.

(8) According to the identified minimum initiating charge, 50 rounds pressed samples were tested for re-checking. At this point, the sample should be fully exploded.

For example, the measurement results of minimum initiating charge in Example 1 are shown in Table 1:

TABLE 1

| Primer charge | Initiating results | Ratio of full or half explosion |
|---|---|---|
| 150 mg | Full explosion | 10/10 |
| 140 mg | Full explosion | 10/10 |
| 130 mg | Full explosion | 10/10 |
| 125 mg | Full explosion | 10/10 |
| 120 mg | Half explosion or no explosion | 6/10 |

From the above Table 1, the minimum initiating charge of Example 1 was found to be 120 mg under the above test conditions. In the present measurement, the minimum initiating charge of each of Examples 1-9 was measured, wherein at least 5 kinds of primer charges were selected for each of the examples, and each of the primer was charged for 10 rounds, and the results are shown in Table 2 below.

[Determination of Thermal Decomposition Temperature]

The thermal decomposition temperatures of the compounds of Examples 1-9 were measured in the temperature range of 50° C. to 250° C. under 10° C.·min⁻¹ heating rate and 20 mL·min⁻¹ nitrogen flow rate, using TGA/DSC 3+ Synchronous Thermal Analyzer (METTLER TOLEDO AG), and the results are shown in Table 2 below.

[Determination of Density]

The densities of the compounds of Examples 1-9 were measured at 25° C. using a Micromeritics Accupyc II 1340 pycnometer, and the results are shown in Table 2 below.

[Determination of Angles of Repose]

Figure 29:
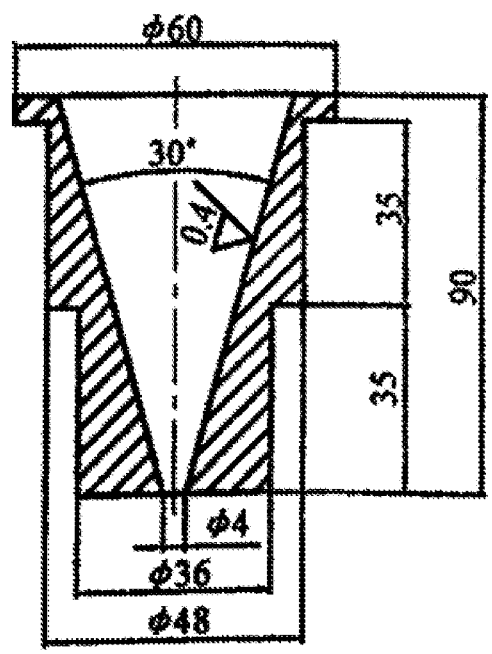
FIG. 29 is a schematic diagram of the funnel used for the determination of the angle of repose of a compound of the present invention.
Figure 30:
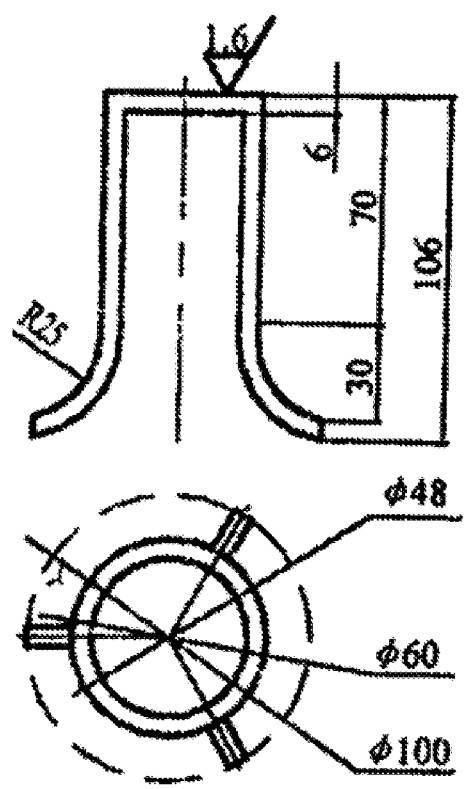
FIG. 30 is a schematic diagram of the three scaffolds used for the determination of the angle of repose of a compound of the present invention.

The test was performed according to the following steps:

(1) A funnel made of metal (such as copper H62) with a smooth surface and an angle of 30°, inner diameter of the outlet of 4 mm, a deburred outer surface, a chrome-plated inner surface, and radius R=1~2 as shown in FIG. 29 was provided; the three brackets of metal material shall be designed so that the distance from the exit end face of the funnel to the measuring surface is 36 mm, as shown in FIG. 30.

(2) The tested compound (the tested objects of the compounds in Examples 1-9) were dried according to the corresponding regulations, and after the technical requirements were met, it was naturally cooled in a dryer for 30 minutes for later use.

(3) A piece of measuring coordinate paper (for example, the size of 150 mm×150 mm) was behind the shielding panel; the funnel is sleeved on the bracket, to be in the center of the measuring coordinate paper.

(4) 3 g of the treated tested compounds were weighed to the nearest 0.1 g with a plate balance (for example, a maximum weighing of 200 g and a graduation value of 0.1 g), and placed in a paper dustpan for later use.

Then the test was performed according to the steps below:

(1) Behind the shielding panel, the tested compounds in the paper dustpan were poured into the funnel slowly along the wall, so that the agents fell freely on the measuring coordinate paper to form a cone.

(2) The funnel and its bracket were removed, and the cone height was measured to the nearest 1 mm using a height vernier caliper (for example, measuring range from 0 mm to 150 mm, graduation value 0.02 mm).

(3) The end points of the two diameters perpendicular to each other at the bottom surface of the cone on the measuring coordinate paper were marked with a pencil.

(4) The compounds on the measuring coordinate paper were poured back into the paper dustpan, and lengths of the two diameters perpendicular to each other marked on the measurement coordinate paper were read to the nearest 1 mm, and the arithmetic mean value was taken.

(5) The residual compounds on the funnel and the measuring coordinate paper were swept into the waste cup with a brush.

Thus, the angle of repose can be calculated by the height of the cone and its two diameter lengths by the following formula (1):

$$\theta = \tan^{-1}(2h/D) \qquad \text{Formula(1)}$$

Wherein θ is the angle of repose of the tested agent, h is the height of the cone, and D is the arithmetic mean of the two diameters perpendicular to each other at the bottom surfaces of the cones. The results of the calculated angle of repose are shown in Table 2 below.

The minimum initiating charge I, thermal decomposition temperature, density and angle of repose of each of the examples obtained in the above-mentioned determinations are shown in Table 2 as follows:

TABLE 2

| | Minimum initiating charge | Thermal decomposition temperature | Density | Angle of repose |
|---|---|---|---|---|
| Example 1 | 125 mg | 161° C. | 1.83 g/cm³ | 31.2° |
| Example 2 | 120 mg | 182° C. | 1.83 g/cm³ | 32.2° |
| Example 3 | 125 mg | 190° C. | 1.89 g/cm³ | 32.5° |
| Example 4 | 130 mg | 197° C. | 1.82 g/cm³ | 31.7° |
| Example 5 | 120 mg | 180° C. | 1.87 g/cm³ | 33.3° |
| Example 6 | 135 mg | 184° C. | 1.83 g/cm³ | 32.1° |
| Example 7 | 100 mg | 160° C. | 1.88 g/cm³ | 30.2° |
| Example 8 | 120 mg | 163° C. | 1.81 g/cm³ | 31.8° |
| Example 9 | 140 mg | 188° C. | 1.87 g/cm³ | 34.1° |

In general, it is preferred to have a higher decomposition temperature, a larger density, and a smaller angle of repose. However, the invention is not limited thereto.

[Determination of Minimum Initiating Charge II]

Performed in accordance with the standards set forth in GJB 5891-2006; specifically, followed these steps:

(1) 600 mg of RDX was pressed into three standard 8# detonators at different pressures by three times, each charge was about 200 mg, 200 mg, and 200 mg, so that the charge density was 1.65-1.75 g/cm³, 1.6-1.68 g/cm³ and 1.5-1.6 g/cm³ from bottom to top.

(2) A certain amount of the compound of Example 1 was used as a primer at a pressure of 14.28 MPa, and pressed into the uppermost layer of the detonator.

(3) The reinforced cap was pressed onto it and the electric ignition head was installed for sealing.

(4) The installed detonator was placed on a lead plate approximately 5 mm in thickness, and then connected to the electric ignition device.

(5) The ignition device was started to observe if the detonator was successfully detonated and the lead plate was broken down. Here, "successful detonation" meant that the three layers of RDX charge were all detonated without white powder remains, and the lower lead plate was broken down, and the diameter of the blast hole was larger than the diameter of the detonator.

Wherein, in the present measurement, a total of at least five kinds of primer charges were selected for Example 1, and each of the primer charges was filled with 10 rounds. Therefore, the minimum initiating charge of the compound of Example 1 was measured as 50 mg (52.11 MPa, 1.75 g/cm³, 8# detonator).

[Other Initiation Tests]

The compound of Example 1 as a primer, under the pressure of 15 MPa-50 MPa, 500 mg of RDX and PETN can be stably detonated with the sample obtained by pressing 8# detonator less than 150 mg, and a blast hole with a diameter of 8-15 mm was formed on the 5 mm lead plate. In other words, its initiation capability was strong, about 2-3 times that of DDNP.

Further, the compound of Example 1 had a calculated detonation velocity and detonation pressure equivalent to HMX at a charge density of 1.85 g/cm³, and had strong detonation ability.

The above-described embodiments are merely preferred embodiments of the present invention, and the scope of the present invention is not limited thereto, and any insubstantial changes and substitutions made by those skilled in the art based on the present invention are intended to fall within the scope of the present invention as claimed.

What is claimed is:

1. A compound of Formula (F')

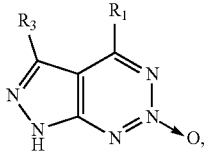

Formula (F')

wherein,
said $R_1$ is selected from the group consisting of —H, —$NH_2$, —$NO_2$, —$NHNO_2$, —$N_3$, —F, —Cl, —Br, —I, and —$C_nH_m(NO_2)_p$, wherein m+p=2n+1, and n=1, 2, 3 or 4; and
said $R_3$ is selected from the group consisting of —H, —$NH_2$, —$NO_2$, —$NHNO_2$, —$N_3$, —F, —Cl, —Br, —I, and —$C_nH_m(NO_2)_p$, wherein m+p=2n+1, and n=1, 2, 3 or 4.

2. The compound of claim 1, wherein the $R_1$ is selected from the group consisting of —$N_3$, —$NO_2$, —Cl, —$NH_2$, and —$NHNO_2$.

3. The compound of claim 1, wherein the $R_3$ is —$NO_2$.

4. The compound of claim 1, wherein
the $R_1$ is selected from the group consisting of —$N_3$, —$NO_2$, —Cl, —$NH_2$, and —$NHNO_2$; and
the $R_3$ is —$NO_2$.

5. The compound of claim 1, wherein the $R_1$ is —$N_3$.

6. The compound of claim 1, of Formula (F)

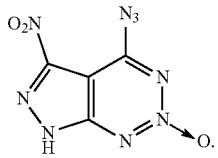

Formula (F)

7. A method of preparing the compound of claim 6, comprising:
mixing 3-amino-4-[1H-tetrazole]-1H-pyrazole, a first salt, and a first azide, to obtain a first mixture;
mixing the first mixture and a first acid, to obtain a first compound; and
mixing the first compound and a first nitrating reagent, wherein,
the first salt is at least one selected from the group consisting of: ammonium chloride, aluminum chloride, triethylamine hydrochloride and cobaltous chloride;
the first azide is at least one selected from the group consisting of: sodium azide and ammonium azide;
the first acid is at least one selected from the group consisting of: hydrochloric acid, acetic acid, formic acid, acetic anhydride, trifluoroacetic acid and sulfuric acid; and
the first nitrating reagent is at least one selected from the group consisting of: a combination of 100% nitric acid and trifluoroacetic anhydride, a combination of 100% nitric acid and concentrated sulfuric acid, fuming nitric acid, nitronium tetrafluoroborate, and nitrogen pentoxide.

8. The method of claim 7, wherein the method comprises:
mixing 3-amino-4-[1H-tetrazole]-1H-pyrazole, ammonium chloride, and sodium azide, to obtain the first mixture;
mixing the first mixture and hydrochloric acid, to obtain the first compound; and
mixing the first compound, 100% nitric acid and trifluoroacetic anhydride.

9. The method of claim 7, wherein the method comprises:
mixing 3-amino-4-[1H-tetrazole]-1H-pyrazole, aluminum chloride, and sodium azide, to obtain the first mixture;
mixing the first mixture, acetic acid, and formic acid, to obtain the first compound; and
mixing the first compound, 100% nitric acid, and trifluoroacetic anhydride.

10. The method of claim 7, wherein the method comprises:
mixing 3-amino-4-[1H-tetrazole]-1H-pyrazole, triethylamine hydrochloride, and sodium azide, to obtain the first mixture;
mixing the first mixture, and acetic anhydride, to obtain the first compound; and
mixing the first compound, and nitronium tetrafluoroborate.

11. The method of claim 7, wherein the method comprises:
mixing 3-amino-4-[1H-tetrazole]-1H-pyrazole, cobaltous chloride, and sodium azide, to obtain the first mixture;
mixing the first mixture and trifluoroacetic acid, to obtain the first compound; and
mixing the first compound, and nitrogen pentoxide.

12. A method of preparing an explosive, comprising using the compound according to claim 1 as an ingredient of the explosive.

13. The method of claim 12, wherein the explosive is a primer.

14. An explosive, comprising the compound according to claim 1.

15. The explosive of claim 14 wherein the explosive is a primer.

* * * * *